United States Patent
Ikeda et al.

(10) Patent No.: US 10,765,405 B2
(45) Date of Patent: Sep. 8, 2020

(54) ULTRASOUND IMAGING PICKUP APPARATUS

(71) Applicant: Hitachi, Ltd., Tokyo (JP)

(72) Inventors: Teiichiro Ikeda, Tokyo (JP); Hiroshi Masuzawa, Tokyo (JP); Shinta Takano, Tokyo (JP); Chizue Ishihara, Tokyo (JP); Mayumi Suzuki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 898 days.

(21) Appl. No.: 15/306,851

(22) PCT Filed: Apr. 22, 2015

(86) PCT No.: PCT/JP2015/062306
§ 371 (c)(1),
(2) Date: Oct. 26, 2016

(87) PCT Pub. No.: WO2015/166869
PCT Pub. Date: Nov. 5, 2015

(65) Prior Publication Data
US 2017/0042509 A1 Feb. 16, 2017

(30) Foreign Application Priority Data

Apr. 28, 2014 (JP) .................................. 2014-092630

(51) Int. Cl.
*A61B 8/00* (2006.01)
*A61B 8/14* (2006.01)
(Continued)

(52) U.S. Cl.
CPC .............. *A61B 8/4488* (2013.01); *A61B 8/00* (2013.01); *A61B 8/14* (2013.01); *A61B 8/145* (2013.01);
(Continued)

(58) Field of Classification Search
CPC .......... A61B 8/4488; A61B 8/00; A61B 8/14; A61B 8/5269; A61B 8/145; A61B 8/5207;
(Continued)

(56) References Cited

U.S. PATENT DOCUMENTS

| 8,485,977 B2 | 7/2013 | Hirama |
| 2009/0326377 A1 | 12/2009 | Hirama |
| 2016/0174938 A1 | 6/2016 | Takano |

FOREIGN PATENT DOCUMENTS

| JP | 10-277042 A | 10/1998 |
| JP | 2009-240700 A | 10/2009 |
| WO | 2015/025655 A1 | 2/2015 |

OTHER PUBLICATIONS

International Preliminary Report on Patentability received in corresponding International Application No. PCT/JP2015/062306 dated Nov. 10, 2016.

(Continued)

*Primary Examiner* — Elmer M Chao
(74) *Attorney, Agent, or Firm* — Mattingly & Malur, PC

(57) ABSTRACT

Reception beamforming that does not generate discontinuity in the vicinity of the depth of a transmit focus is executed even if reception scanning lines are disposed outside of the irradiation area of a focusing-type transmission beam. The degree of discontinuity showing the discontinuity of reception signals detected by plural ultrasound elements 105 or the degree of discontinuity regarding the discontinuity of the wave fronts of phased signals is detected by a discontinuity extracting unit 113. If there is an area where the degree of discontinuity is larger than a predefined value, a delay time generating unit 114 for discontinuity elimination changes the delay times in the area where the discontinuity is generated.

13 Claims, 16 Drawing Sheets

(51) Int. Cl.
  *G01S 15/89*   (2006.01)
  *G10K 11/34*   (2006.01)
  *G01S 7/52*    (2006.01)
  *A61B 8/08*    (2006.01)
  *G01N 29/26*   (2006.01)
(52) U.S. Cl.
  CPC .......... *A61B 8/5207* (2013.01); *A61B 8/5269* (2013.01); *G01N 29/262* (2013.01); *G01S 7/5205* (2013.01); *G01S 7/52085* (2013.01); *G01S 15/8915* (2013.01); *G01S 15/8997* (2013.01); *G10K 11/346* (2013.01)
(58) Field of Classification Search
  CPC ............ G61S 15/8997; G61S 15/8915; G01N 29/262; G01S 7/52085; G01S 7/5205; G10K 11/346
  See application file for complete search history.

(56) References Cited

OTHER PUBLICATIONS

International Search Report of PCT/JP2015/062306 dated Jul. 7, 2015.

FIG. 3
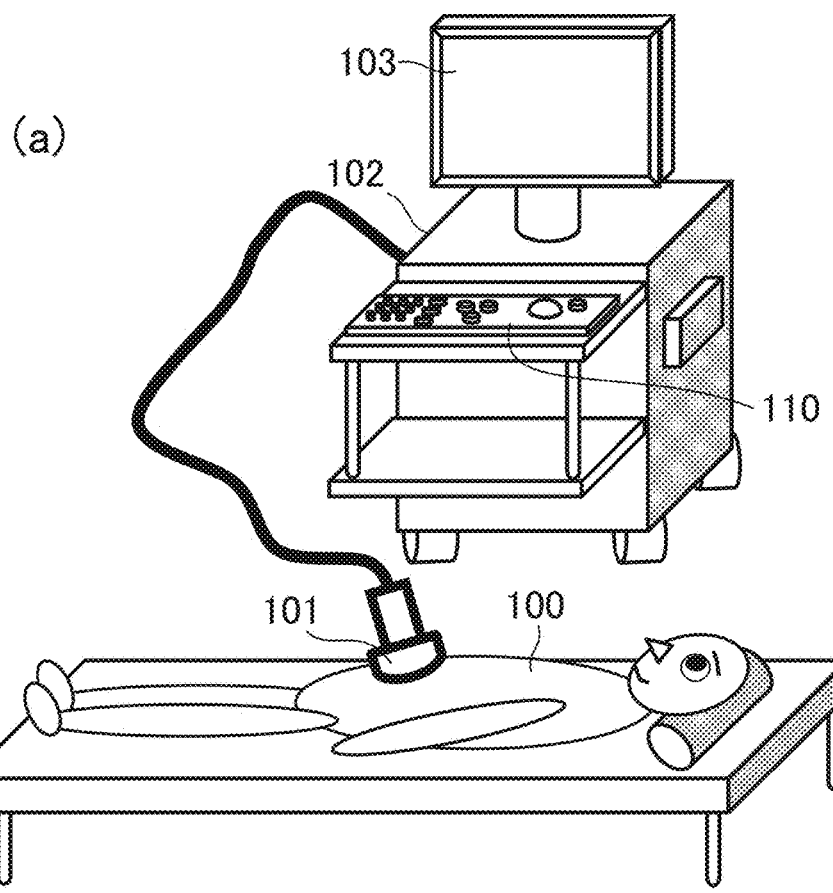
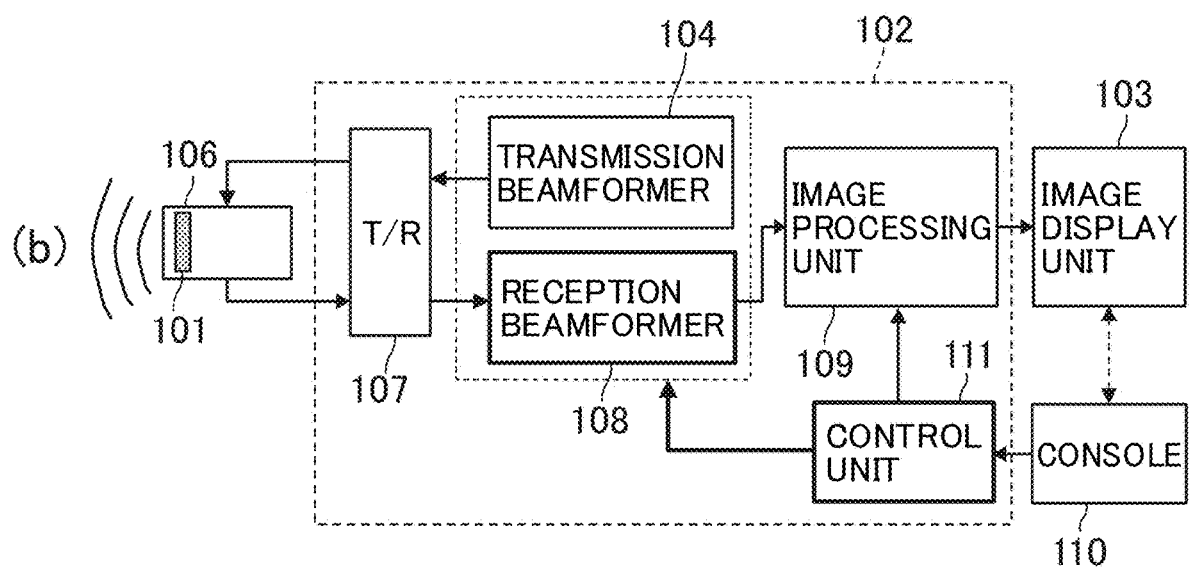

FIG. 5
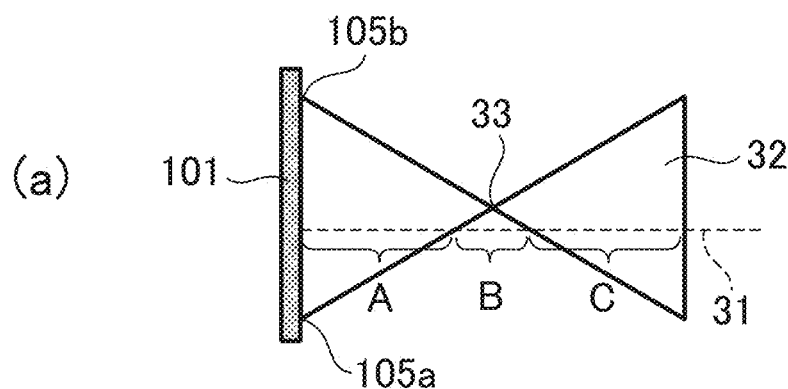
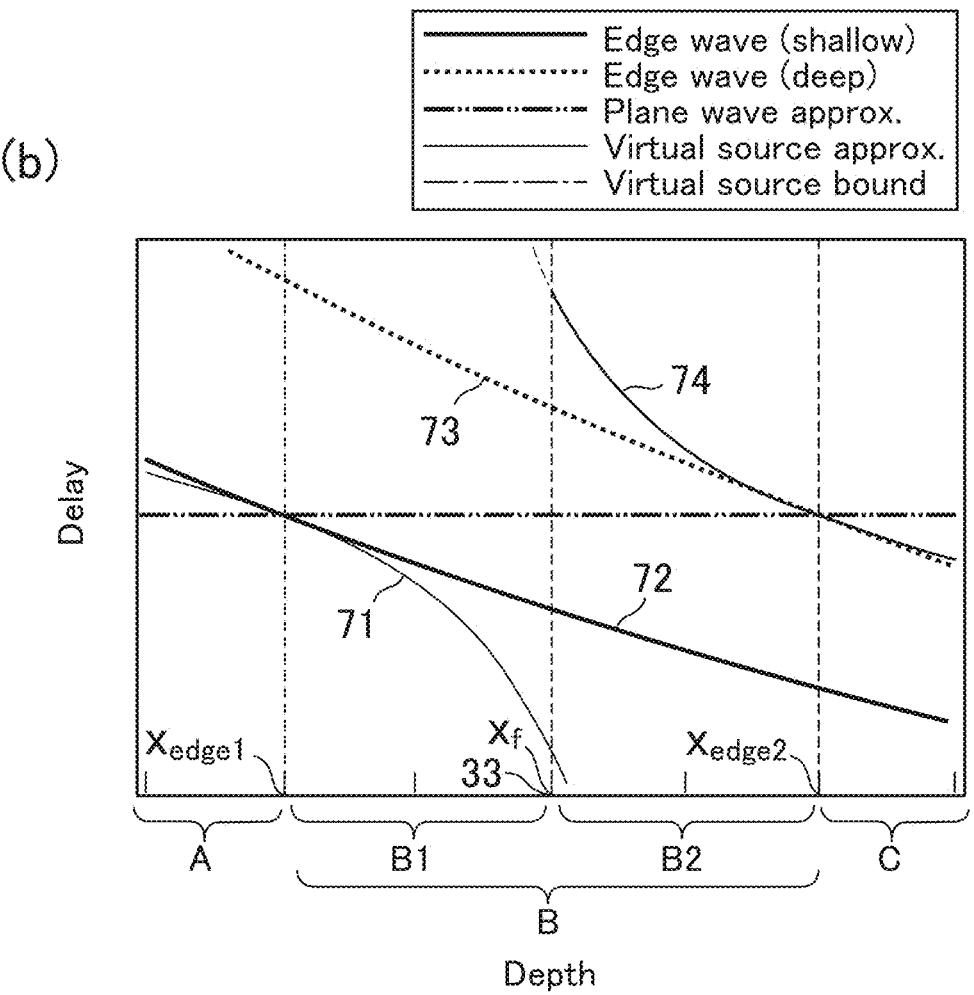

FIG. 7
(a)
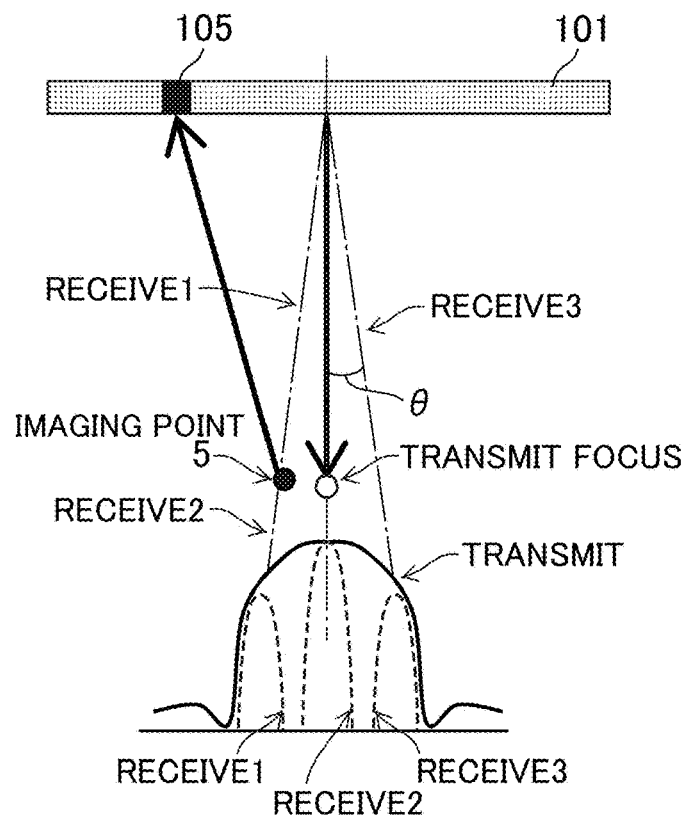
(b)
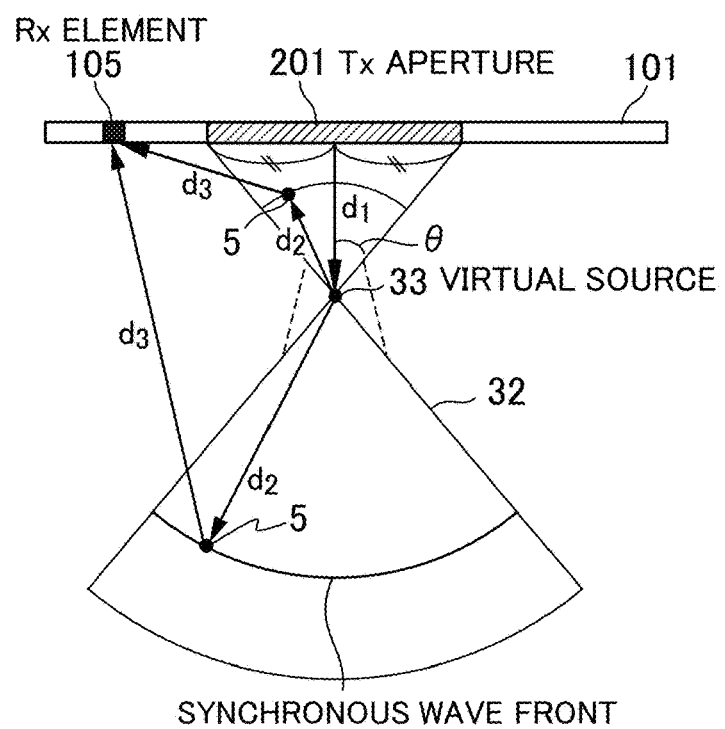

FIG. 11
(a)
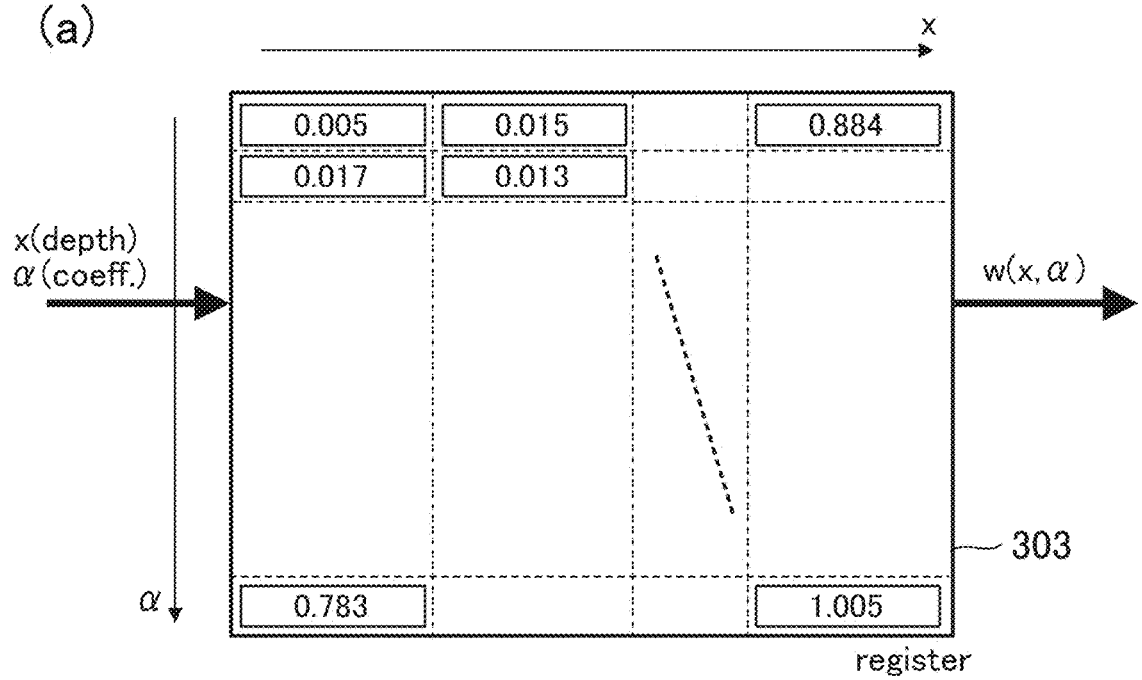
(b)
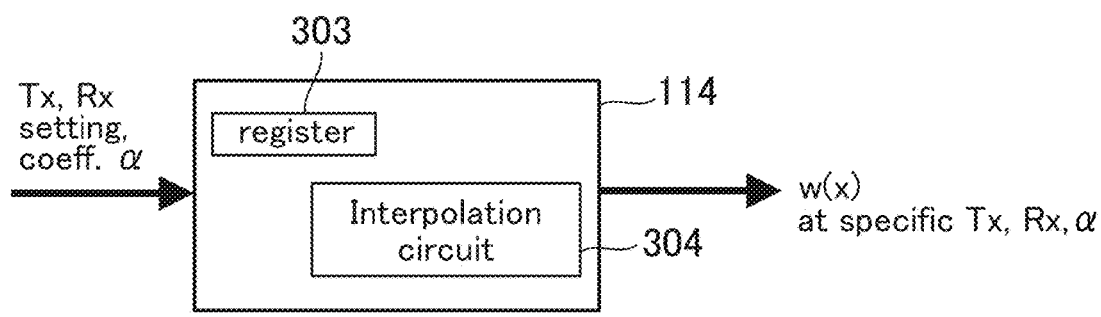
(c)
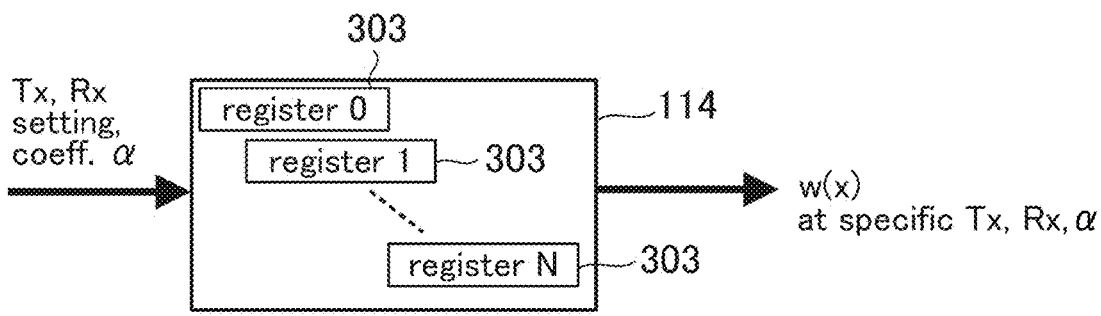

FIG. 15
(a)
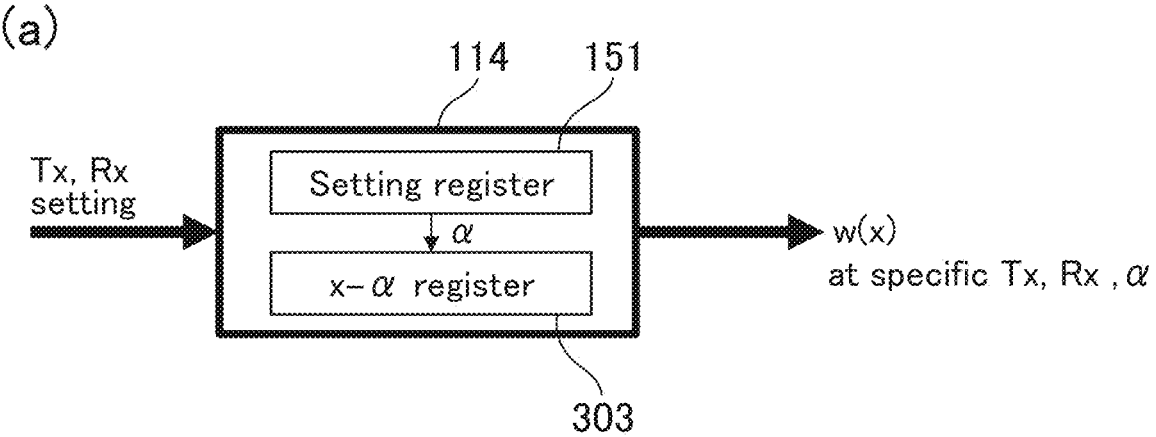
(b)
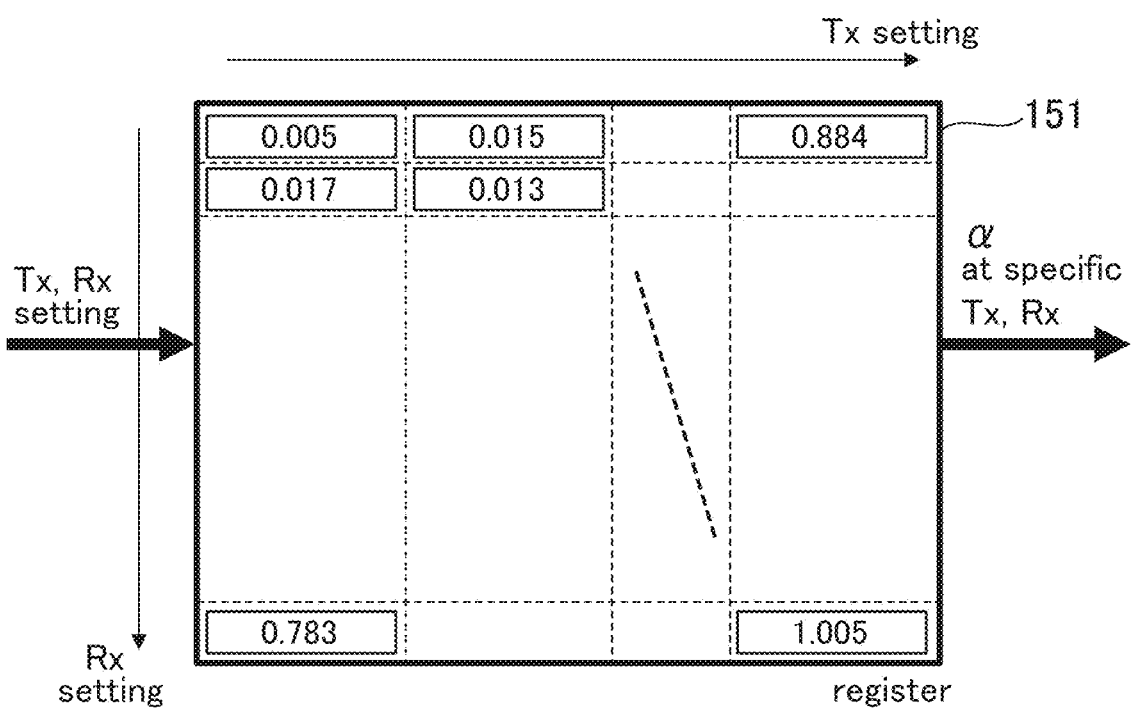

ULTRASOUND IMAGING PICKUP APPARATUS

TECHNICAL FIELD

The present invention relates to an ultrasound imaging technology that takes images inside of a test object using ultrasound waves.

BACKGROUND ART

The ultrasound imaging technology is a technology that takes images of the inside of a test object such as a human body noninvasively using ultrasound waves (inaudible sound waves, that is, sound waves whose frequencies are typically 20 kHz or higher).

As a transmission method for transmitting an ultrasound beam from an ultrasound probe to a test object such as a human body, there are two kinds of transmission methods, and one is a dispersing-type transmission method in which an ultrasound beam that disperses in a fan shape is transmitted, and another is a focusing-type transmission method in which the transmit focus of an ultrasound beam is disposed inside of a test object, and the ultrasound beam is converged on the focus.

Because the transmission/reception of ultrasound waves by an ultrasound image pickup apparatus is performed by means of an array with an aperture of a finite diameter, the transmission or reception is affected by the diffractions of the ultrasound waves caused by the edge of the aperture, therefore it is difficult to improve the resolution in the direction of an azimuthal angle. The above problem can be solved if an array of an infinite length can be prepared, but in actuality it is impossible to prepare an array of an infinite length. Therefore, in order to improve the resolution in the direction of an azimuthal angle, channel domain phasing technologies have been widely studied in recent years, with the result that new phasing schemes such as an adaptive beamformer and aperture synthesis have been extensively reported.

The aperture synthesis will be briefly explained. First, by respectively giving delay times to reception signals received by plural elements included in an ultrasound probe, the delayed reception signals are virtually focused on a certain point, and then a phased signal is obtained by adding these delayed reception signals. The aperture synthesis is performed by synthesizing this phased signal and one phased signal or more obtained regarding the same point through other one or more transmissions/receptions, and by superimposing these signals on each other.

In the aperture synthesis, because phased signals obtained by an ultrasound probe through the transmission/reception to or from different directions regarding a certain point can be superimposed on each other, it can be expected that the improvement of the resolution of a point image and the robustness against the inhomogeneity of the point image are provided. In addition, because processing gain can be increased owing to the superimposing processing, the number of transmissions of ultrasound waves can be reduced in comparison with the number of usual transmissions of ultrasound waves, the aperture synthesis can be also applied to high-speed imaging.

Patent Literature 1 relates to an ultrasound diagnostic apparatus, and discloses a technology in which aperture synthesis is performed using an improved virtual source method in ultrasound imaging in which focusing-type transmission is performed. To put it concretely, the aperture synthesis is performed under the assumption that a focus is a virtual source in an area where the energy of an ultrasound beam is converged on a focus (an area A shown in FIG. 2 of Patent Literature 1), while the aperture synthesis is performed under the assumption that a spherical wave is irradiated from the end of a probe in areas which are adjacent to the area A and in which the energy of the ultrasound beam disperses (areas B and C).

CITATION LIST

Patent Literature

Patent Literature 1: Japanese Unexamined Patent Application Publication No. Hei 10 (1998)-277042

SUMMARY OF INVENTION

Technical Problem

The focusing-type transmission method has smaller errors between delay times even in the case where the divergence angle of transmission is large in comparison with the dispersing-type transmission method. Therefore, in the focusing-type transmission method, because the divergence angle of the transmitted ultrasound wave can be set large, a larger number of reception scanning lines (assemblies of points at which phased signals are calculated) can be set in comparison with in the dispersion-type transmission method. It becomes possible to speedily image a wider imaged area with a fewer number of transmissions by setting a many number of reception scanning lines. Furthermore, in transmission aperture processing, more phased signals can be synthesized in the case of a large number of reception scanning lines being set than in the case of a small number of reception scanning lines being set even if the same number of transmissions are performed in both cases, and advantageous effects such as the improvement of resolution can be obtained.

As shown in Patent Literature 1, delay times are calculated in the irradiation area of a transmission beam (in an area where ultrasound energy is converged) using the virtual source method, and delay times are calculated under the assumption that a spherical wave is irradiated from the end of a probe outside of the irradiation area of the transmission beam (in areas where the energy of the ultrasound beam disperses), which makes it possible to obtain phased signals even at points outside of the irradiation area of the transmission beam. Therefore, reception scanning lines can be set even outside of the irradiation area of the transmission beam.

However, in the case where delay times at points on a reception scanning line outside of the irradiation area of the transmission beam are calculated using the waveform of a spherical wave which is considered to be irradiated from the end of the probe according to the technology disclosed in Patent Literature 1, the waveform of the spherical wave used for calculation of the delay times have to be switched from the waveform of a spherical wave irradiated from the left part of the edge of the probe to the waveform of a spherical wave irradiated from the right part of the edge of the probe or vice versa in the vicinity of the depth of a transmit focus. Owing to this switching, there arises a problem in that a curve representing the variation between delay times in the direction of the depth along the reception scanning line becomes discontinuous in the vicinity of the depth of the transmit focus. The discontinuity of the variation between the delay times in the vicinity of the depth of the transmit focus incurs the discontinuity of the pixel values of a generated ultrasound image in the vicinity of the depth of the transmit focus, so that an artifact is generated in the vicinity of the depth of the transmit focus.

One of the objects of the present invention is to execute reception beamforming that does not generate discontinuity in the vicinity of the depth of the transmit focus even if reception scanning lines are disposed outside of the irradiation area of a focusing-type transmission beam.

Solution to Problem

In a first embodiment of the present invention, a discontinuity extracting unit detects the degree of discontinuity showing the discontinuity of the wave fronts of reception signals received by plural ultrasound elements or the discontinuity of the wave fronts of phased signals. If there is an area where the degree of discontinuity is larger than a predefined value, a delay time generating unit for discontinuity elimination changes delay times in the area where the discontinuity is generated.

An ultrasound image pickup apparatus according to a second embodiment of the present invention includes: an ultrasound element array in which plural ultrasound elements are arranged in a predefined direction; a transmission beamformer that makes at least some of the plural ultrasound elements transmit a focusing-type transmission beam to the imaged area of a test object; and a reception beamformer that delays reception signals output by the plural ultrasound elements, which receive ultrasound waves from the test object, by delay times to phase the reception signals, and outputs phased signals after adding the delayed and phased reception signals. The reception beamformer includes: a scanning line setting unit that sets reception scanning lines not only inside of the irradiation area of the focusing-type transmission beam but also outside of the irradiation area of the focusing-type transmission beam; and a delay time calculation unit that calculates delay times at predefined points on the reception scanning lines. The delay time calculation unit calculates delay times on the reception scanning lines outside of the irradiation area in a shallow area on the shallow side of the transmit focus of the transmission beam on the basis of the waveform of a diffracted wave from one end of the plural ultrasound elements that irradiate the transmission beam, and calculates delay times on the reception scanning lines outside of the irradiation area in a deep area on the deep side of the transmit focus of the transmission beam on basis of the waveform of a diffracted wave from the other end. Furthermore, the delay time calculation unit includes a delay time generating unit for discontinuity elimination for generating delay times that connects the delay times in the shallow area and the delay times in the deep area in the vicinity of the transmit focus.

Advantageous Effects of Invention

According to the present invention, reception beamforming that does not generate discontinuity in the vicinity of the depth of a transmit focus can be executed even if reception scanning lines are disposed outside of the irradiation area of a focusing-type transmission beam.

BRIEF DESCRIPTION OF DRAWINGS

FIGS. 3(a) and (b) are a perspective view and a block diagram of the ultrasound image pickup apparatus of the second embodiment respectively.

FIG. 5(a) is an explanatory diagram showing that a reception scanning line 31 is divided into areas A to C depending on the positional relationship between the reception scanning line 31 and the irradiation area 32 of a transmission beam, and (b) is a graph showing the curves of delay times calculated from the wave fronts in the respective areas A to C.

FIG. 7(a) is an explanatory diagram for explaining beamforming by means of a dispersing-type transmission beam, and (b) is an explanatory diagram for explaining beamforming by means of a focusing-type transmission beam.

FIG. 11(a) is a block diagram showing a register configuration for realizing the operation of the delay time generating unit 114 for discontinuity elimination of the second embodiment in a hardware-based way, (b) is a block diagram showing an example for configuring the delay time generating unit 114 for discontinuity elimination using a register and an interpolation circuit, and (c) is a block diagram showing an example for configuring the delay time generating unit 114 for discontinuity elimination using plural registers.

FIG. 15(a) is an explanatory diagram showing an example of a register 151 that configures an optimal coefficient setting unit 113B of the fourth embodiment and that is disposed in the delay time generating unit 114 for discontinuity elimination, and (b) is an explanatory diagram showing a register 151 that configures an optimal coefficient setting unit 113b of the fourth embodiment.

DESCRIPTION OF EMBODIMENTS

Figure 1:
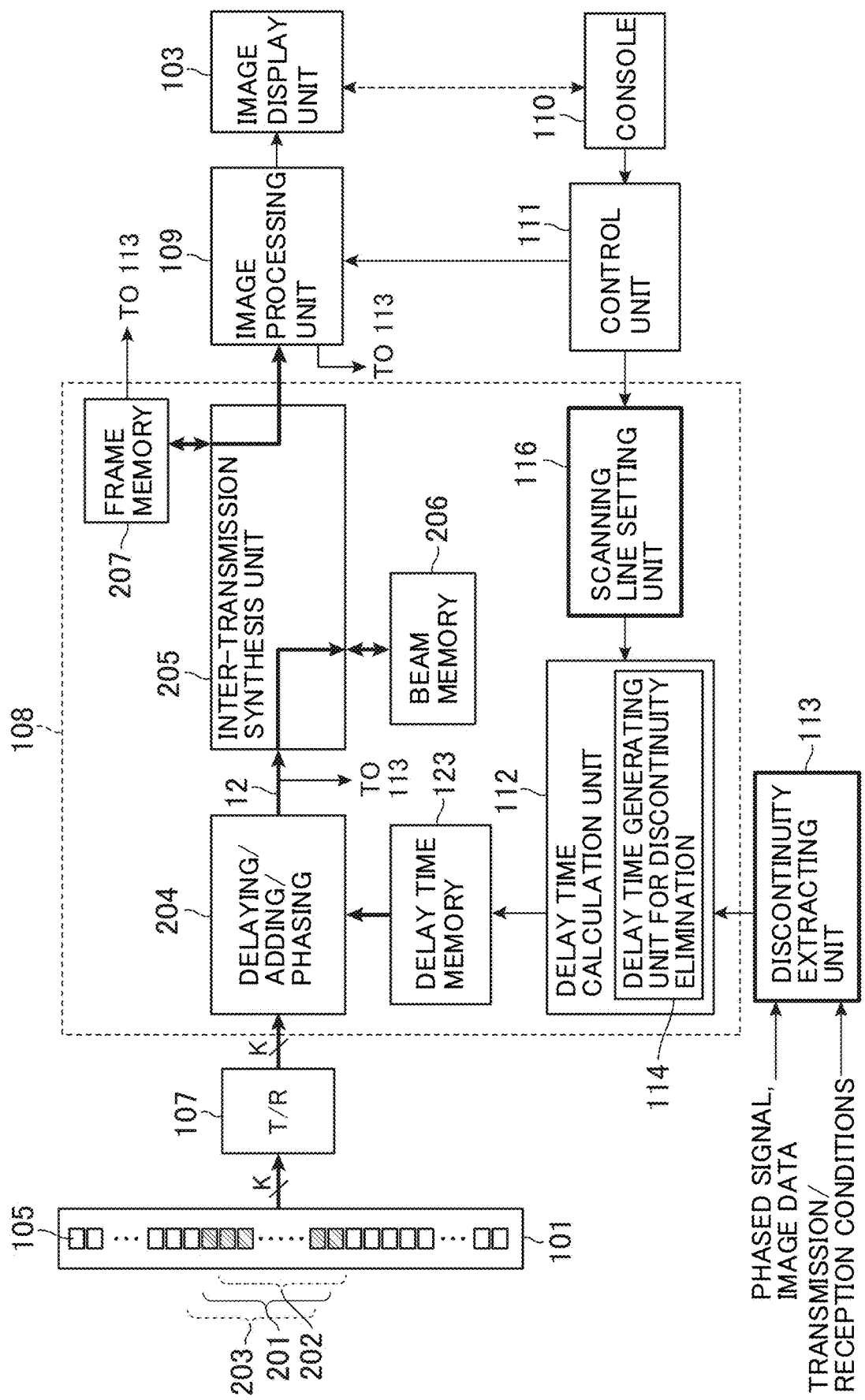
FIG. 1 is a block diagram showing the configuration of the reception beamformer of an ultrasound image pickup apparatus of a first embodiment.

Hereinafter, an ultrasound image pickup apparatus of one embodiment according to the present invention will be explained.

First Embodiment

An ultrasound image pickup apparatus of a first embodiment will be explained with reference to FIG. 1.

The ultrasound image pickup apparatus of the first embodiment includes: a reception beamformer 108 that delays reception signals, which are received by plural ultrasound elements 105, by delay times at respective predefined points on reception scanning lines, phases the delayed reception signals, and then adds these signals to get phased signals 12; a discontinuity extracting unit 113; and a delay time generating unit 114 for discontinuity elimination. The discontinuity extracting unit 113 detects the degree of discontinuity showing the discontinuity of the wave fronts of the phased signals 12. If there is an area where the degree of discontinuity is larger than a predefined value, the delay time generating unit 114 for discontinuity elimination changes delay times in the area where the discontinuity is generated.

As mentioned above, in the first embodiment, whether or not there is an area where the discontinuity of phased signals is generated owing to the discontinuity of delay times is detected from the degree of the discontinuity of the phased signals. If there is an area where discontinuity is generated, the discontinuity of the phased signal can be controlled by changing delay times in the area. Therefore, even in the case where a focusing-type transmission beam is transmitted and reception scanning lines are disposed outside of the irradiation area of the transmission beam, reception beamforming that does not generate discontinuity in the vicinity of the depth of the transmit focus of the focusing-type transmission beam can be executed.

In addition, using image data generated from phased signals, the discontinuity extracting unit 113 can detect discontinuity in the image data.

Although FIG. 1 includes configurations other than the configurations described above, these configurations are the same as configurations used in a second embodiment, and therefore descriptions about them has been omitted above.

Second Embodiment

Figure 2:
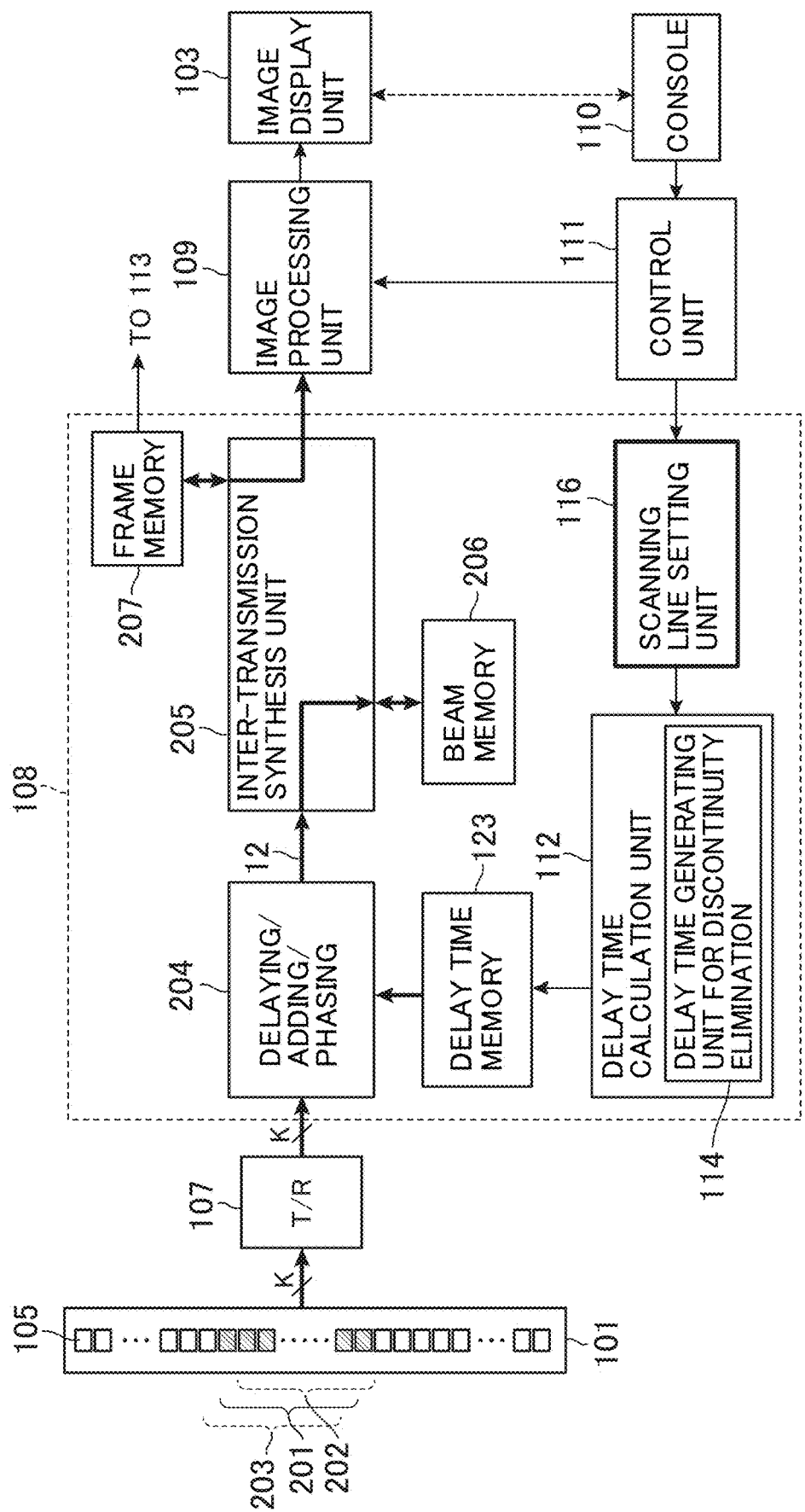
FIG. 2 is a block diagram showing the configuration of the reception beamformer of an ultrasound image pickup apparatus of a second embodiment.

An ultrasound image pickup apparatus of a second embodiment will be explained with reference to FIG. 2, FIGS. 3(a) and (b). FIG. 2 is a block diagram showing a part of the apparatus, FIG. 3(a) is a perspective view of the apparatus, and FIG. 3(b) is a block diagram showing the schematic configuration of the entirety of the apparatus.

As shown in FIG. 2, FIGS. 3(a) and (b), the ultrasound image pickup apparatus of the second embodiment includes: an ultrasound element array 101 in which plural ultrasound elements 105 are arranged in a predefined direction; a transmission beamformer 104 that makes at least apart (201, 202, and 203) of the plural ultrasound elements 105 transmit a focusing-type transmission beam to the imaged area of a test object 100; a reception beamformer 108 that delays reception signals output by the plural of ultrasound elements 105, which receive ultrasound waves from the test object 100, by delay times to phase the reception signals, and outputs phased signals after adding the delayed and phased reception signals.

Figure 4:
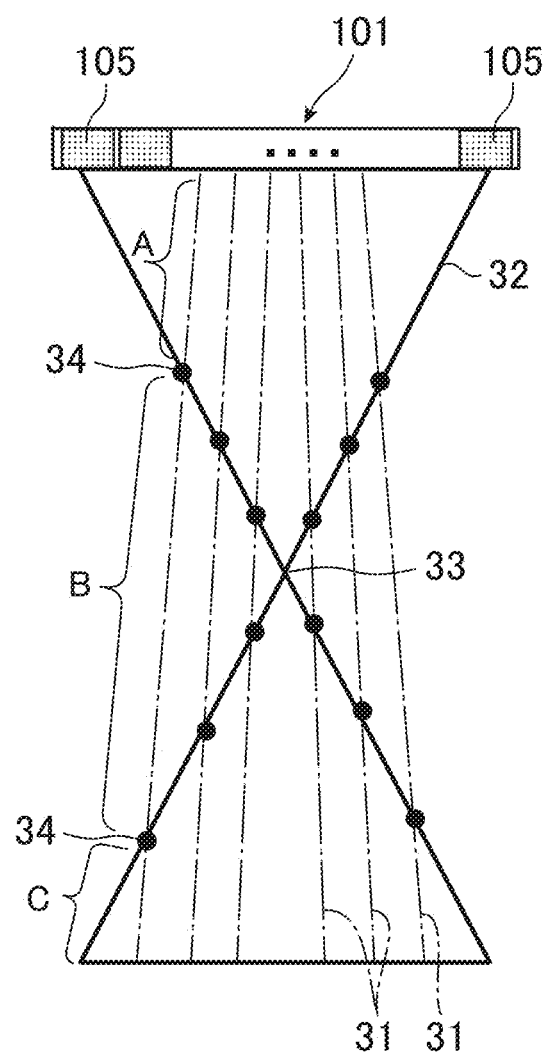
FIG. 4 is an explanatory diagram showing the relationship between the irradiation range 32 of the transmission beam and the reception scanning lines of the second embodiment.

The reception beamformer 108 includes: a scanning line setting unit 116 that sets reception scanning lines 31 not only inside of the irradiation area 32 of the focusing-type transmission beam but also outside of the irradiation area 32 of the focusing-type transmission beam as shown in FIG. 4; and a delay time calculation unit 112 that calculates delay times at predefined points on the reception scanning lines 31.

The delay time calculation unit 112 calculates delay times in an area B (refer to FIG. 4) on reception scanning lines outside of the irradiation area 32. To put it concretely, as shown in FIGS. 5(a) and (b), delay times (shown by a curve 72) are calculated on the basis of the wave shape of a diffracted wave irradiated from one end 105a of the plural ultrasound elements 105, which irradiates the transmission beam, in a shallow area B1 on the shallow side of the transmit focus 33 of the transmission beam. In a deep area B2 on the deep side of the transmit focus 33, delay times (shown by a curve 73) are calculated on the basis of the wave shape of a diffracted wave irradiated from the other end 105b.

Figure 6:
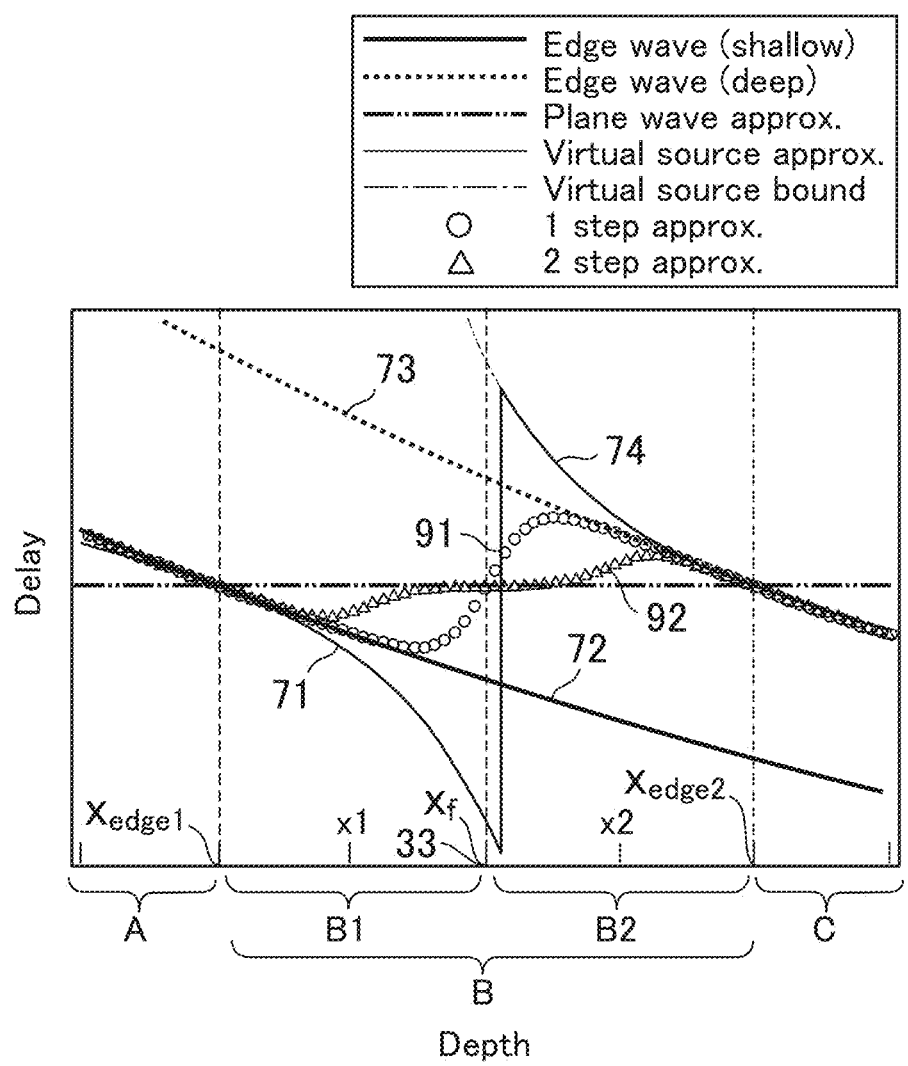
FIG. 6 is a graph showing the curves of delay times calculated from the wave fronts and examples of the shapes of approximating curves 91 and 92 that connect the curves of delay times.

The delay times (shown by the curve 72) of the area B1 and the delay times (shown by the curve 73) of the area B2 are discontinuous with each other as shown in FIG. 5. Therefore, as shown in FIG. 6, the delay time calculation unit 112 includes a delay time generating unit 114 for discontinuity elimination that generates delay times (shown by a curve 91 or a curve 92) that connect the delay times (shown by the curve 72) in the shallow area B1 in the vicinity of the depth of the transmit focus 33 and the delay times (shown by the curve 73) in the deep area B2.

In this way, the delay time generating unit 114 for discontinuity elimination solves a problem in that the curve 72 of the delay times and the curve 73 of the delay times calculated from the diffracted waves in the vicinity of the depth of the transmit focus 33 become discontinuous with each other. With this, even in the case where a focusing-type transmission beam is irradiated and reception scanning lines are disposed outside of the irradiation area of the transmission beam, reception beamforming, which does not generate discontinuity in the vicinity of the transmit focus of the transmission beam, can be executed.

Hereinafter, the ultrasound image pickup apparatus of the second embodiment will be explained more concretely.

The entire configuration of the ultrasound image pickup apparatus will be explained more detailedly with reference to FIG. 2, FIGS. 3(a) and (b).

As shown in FIG. 3(a), the ultrasound image pickup apparatus includes an ultrasound probe 106; an apparatus body 102; an image display unit 103; and a console 110. As shown in FIG. 3(b), the transmission beamformer 104; a transmission/reception separation circuit (T/R) 107; the reception beamformer 108; an image processing unit 109; and a control unit 111 that controls the operations of these components are disposed in the apparatus body 102.

As shown in FIG. 2, the reception beamformer 108 includes: a delay time memory 123; a delaying/adding/phasing unit 204; a beam memory 206; an inter-transmission synthesis unit 205; and a frame memory 207 as well as the abovementioned scanning line setting unit 116; the delay time calculation unit 112; the delay time generating unit 114 for discontinuity elimination.

The transmission beamformer 104 shown in FIG. 3(b) generates a transmission beam signal for generating an ultrasound transmission beam. The transmission beam signal is transferred to the ultrasound probe 106 via the transmission/reception separation circuit 107. The ultrasound probe 106 transfers the transmission beam signal to the respective ultrasound elements 105 of the ultrasound element array 101. The respective ultrasound elements 105 transmit ultrasound waves to the inside of the body of the test object 100. Echo signals reflected in the body are received by the ultrasound element array 101 of the ultrasound probe 106. The received signals pass through the transmission/reception separation circuit 107 again, and phasing/adding calculation processing and the like are executed on the received signals by the reception beamformer 108.

Before the detailed operations of the respective units of the reception beamformer 108 are explained, beamforming executed by means of a typical dispersing-type transmission beam and beamforming executed by means of a typical focusing-type transmission beam will be explained.

FIG. 7(*a*) is a diagram for explaining beamforming by means of an existing dispersing-type transmission beam. In the case where the divergence angle θ of the dispersing-type transmission beam is small, there is not a large difference between the flight travel of an ultrasound wave transmitted from the outermost side of the transmission beam and the flight travel of an ultrasound wave transmitted in the direction of the transmission sound axis. However, in the case where the divergence angle θ of the transmission beam is large, a difference between the flight travel of an ultrasound wave transmitted from the outermost side of the transmission beam and the flight travel of an ultrasound wave transmitted in the direction of a transmission sound axis becomes large. Therefore, because the divergence angle θ of the dispersing-type transmission beam cannot be set very large, it is difficult to set necessary and sufficient number of scanning lines for high-speed imaging and aperture synthesis.

On the other hand, FIG. 7(*b*) is a diagram for explaining beamforming by means of a focusing-type transmission beam. In the irradiation area of the focusing-type transmission beam (an area where ultrasound energy is converged) 32, delay times are calculated using the virtual source method. The procedure for calculating the time of flight (TOF) of a sound wave using the virtual source method will be explained with reference to FIG. 7(*b*). The virtual source method is performed under the assumption that a sound wave is reirradiated in a spherical dispersion fashion from the position of a transmit focus that is regarded as a virtual source. For example, in the case of FIG. 7(*b*), the sound wave travels in the direction of the far side from the virtual source, and travels back in time and returns in the direction of the near side to the ultrasound elements. Here, let's assume that the origin of time (zero time) is set as the time when a sound wave is transmitted from the center position of the transmission aperture (201) of the ultrasound element array 101 (the center between elements in the case where the number of the elements in the transmission aperture are even), and the time of flight tof from the time when the sound wave is transmitted to the time when the sound wave reaches a certain ultrasound element 105 after being reflected at an imaging point (a reception phasing point 5) is given by the next Expression (1). In this Expression, $d_1$ is a distance from the center of the transmission aperture to the virtual source (a focal distance in the case of the focusing-type transmission); $d_2$ is a distance from the virtual source to the reception phasing point 5; $d_3$ is a distance between the reception phasing point 5 and the reception ultrasound element 105; and C is the speed of sound in a medium. In Expression (1), the sign "−" of the double sign ± is adopted in the case where the reception phasing point 5 is at the side of the ultrasound element array 101 viewed from the virtual source, and the sign "+" of the double sign ± is adopted in the case where the reception phasing point 5 is at the opposite side of the ultrasound element array 101 viewed from the virtual source. Here, all the distances d in Expression (1) are scalars.

[Expression 1]

$$tof=(d_1+d_2+d_3)/C \qquad (1)$$

Sign −: in the case where the imaging point is in a transmission irradiation area at the side of the probe.

Sign +: in the case where the imaging point is in a transmission irradiation area at the opposite side of the probe.

Using the virtual source method makes it possible that reception phasing points 5 are set throughout the entire irradiation area 32 of the transmission beam, and a time of flight for each reception ultrasound element 105 is calculated. Furthermore using the calculated times of flight as delay times makes it possible to execute phasing processing. Therefore, in the focusing-type transmission beam, the divergence angle 9 can be set large, and the width of an area within which the sound wave is propagated can be broadened.

However, as shown in FIG. 4(*a*), if plural reception scanning lines 31 are disposed in the entirety of the irradiation area 32 of the focusing-type transmission beam, an area B which passes through the outer side of the irradiation area 32 is generated. In the present invention, as shown in FIG. 8, delay times outside of the irradiation area 32 are calculated under the assumption that spherical waves (diffracted waves) are propagated from ultrasound elements 105*a* and 105*b* at the ends of the transmission aperture 201 of the ultrasound element array 101 that transmits a transmission beam.

For example, as for an area on the left side of the irradiation area 32, it can be considered that a spherical wave (referred to as the diffracted wave hereinafter) 62 irradiated from the ultrasound element 105*a* at the left end is propagated in an area on the shallow side of a transmit focus 33, and it can be also considered that a spherical wave (referred to as the diffracted wave hereinafter) 63 irradiated from the ultrasound element 105*b* at the right end is propagated in an area on the deep side of the transmit focus 33. On the other hand, as for an area on the right side of the irradiation area 32, it can be considered that a diffracted wave 63 irradiated from the ultrasound element 105*b* at the right end is propagated in an area on the shallow side of the transmit focus 33, and it can be also considered that a diffracted wave 62 irradiated from the ultrasound element 105*a* at the left end is propagated in an area on the deep side of the transmit focus 33.

Figure 8:
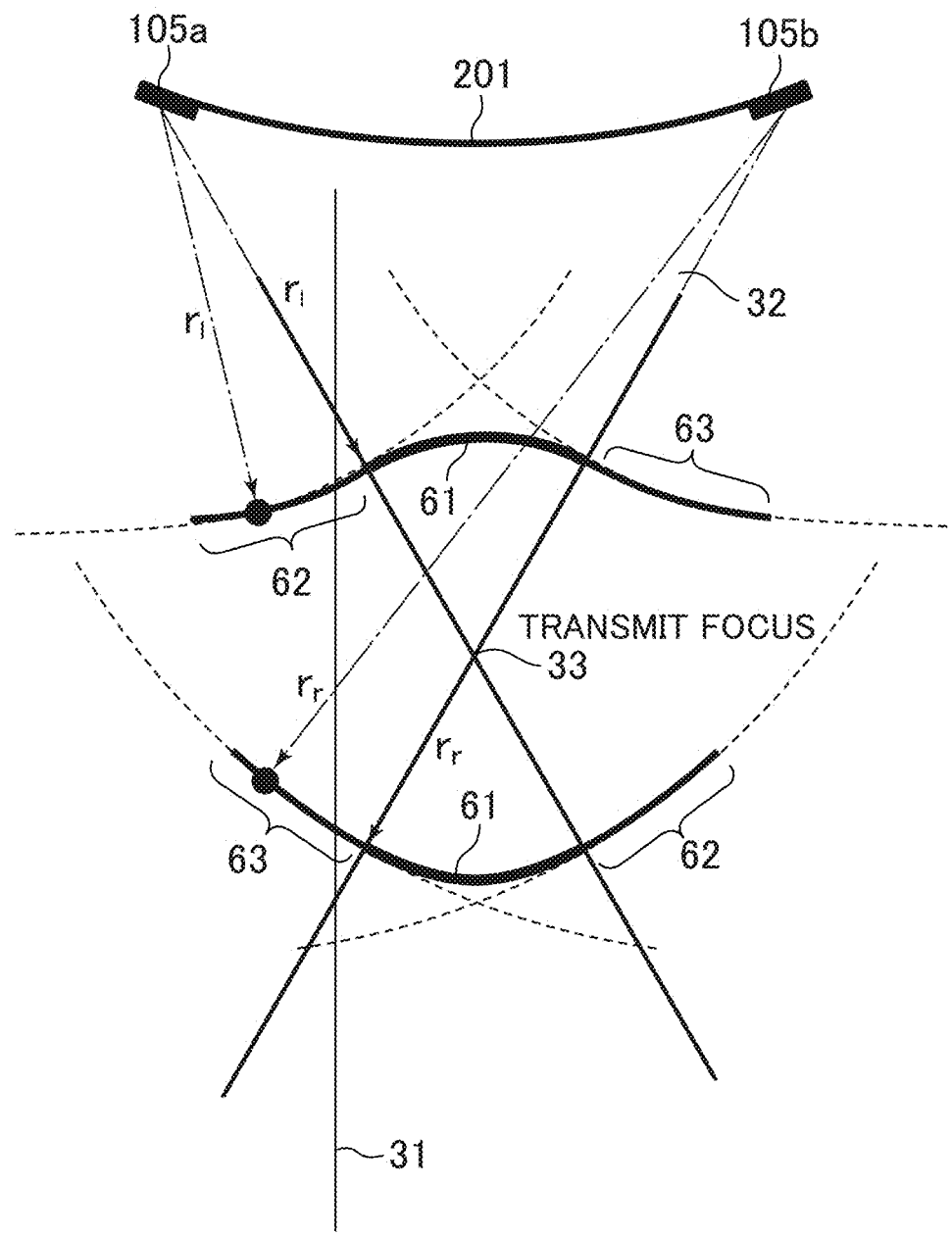
FIG. 8 is an explanatory diagram showing the shapes of wave fronts located inside of and outside of the irradiation area 32 of the focusing-type transmission beam.

As shown in FIG. 8, the shape of a diffracted wave can be geometrically obtained. For example, in an area that is located on the shallow side of the transmit focus 33 and on the left side of the irradiation area 32, the shape of the diffracted wave 62 becomes a circular arc whose center is the ultrasound element 105*a* at the left end and whose radius is $r_1$. In an area that is located on the deep side of the transmit focus 33 and on the left side of the irradiation area 32, the shape of the diffracted wave 62 becomes a circular arc whose center is the ultrasound element 105*b* at the right end and whose radius is $r_r$. Therefore, in the area that is located on the left side of the irradiation area 32, the shape of the diffracted wave is switched from the diffracted wave 62 to the diffracted wave 63 with the vicinity of the transmit focus 33 as a boundary. In the area that is located on the right side of the irradiation area 32, the shape of the diffracted wave is switched from the diffracted wave 63 to the diffracted wave 62 with the vicinity of the transmit focus 33 as a boundary.

Therefore, in the case where a reception scanning line 31 is disposed as shown in FIG. 4 or FIG. 5(a), delay times calculated using the virtual source method are adapted to areas inside of the irradiation areas 32 of the transmission beam (the inner areas A and C), and the curve of the delay times is shown by a curve 71 in the inner area A on the shallow side of the transmit focus 33 (near to the ultrasound element array 101), and shown by a curve 74 in the inner area C on the deep side of the transmit focus 33 as shown in FIG. 5(b). In addition, delay times generated by the diffracted wave 62 is shown by a curve 72 in an area B1, which is located on the shallow side of the transmit focus 33, of the outer area B, and delay times generated by the diffracted wave 63 is shown by a curve 73 in an area B2, which is located on the deep side of the transmit focus 33, of the outer area B.

Figure 9:
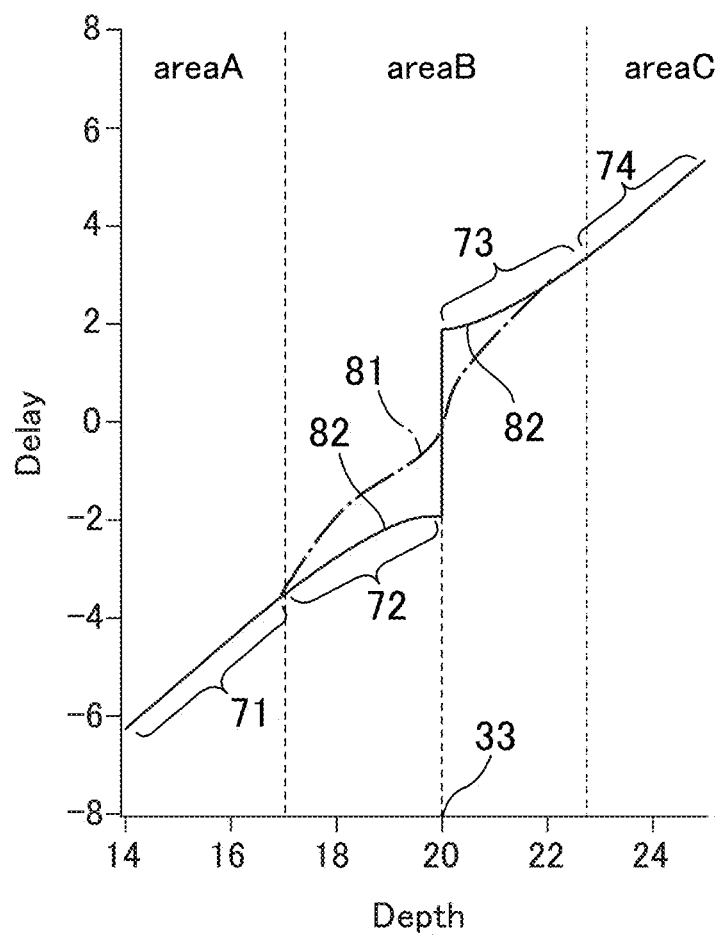
FIG. 9 is a graph showing discontinuous curves 82 calculated from wave fronts and a curve 81 that continuously connects these discontinuous curves.

As is clear from FIG. 5(b), the curve 72 of delay times generated by the diffracted wave 62 and the curve 73 of delay times generated by the diffracted wave 63 do not get contact with each other, and therefore if these curves are adopted as they are, there arises a problem in that the delay times become discontinuous at the transmit focus 33 as shown by solid lines 82 in FIG. 9 (However, the discontinuity between the solid lines 82 is connected by a straight line at the transmit focus 33 as shown in FIG. 9). This discontinuity of the delay times makes phased signals 12 to be generated and the pixel values of an ultrasound image to be generated discontinuous in the vicinity of the depth of the transmit focus 33, so that an artifact is generated.

The delay time generating unit 114 for discontinuity elimination generates delay times that continuously connect these discontinuous delay times. To put it concretely, delay times along a curve that asymptotically approaches the curve 72 or the curve 73 such as a curve 91 or a curve 92 are generated. Herewith, the generated delay times can connect the discontinuity of the delay times in the vicinity of the transmit focus 33 like a curve 81 shown in FIG. 9.

Here, the offset parts of delay times caused by plane wave propagation are subtracted from delay times shown by the vertical axis in a graph shown in FIG. 5(b) or in a graph shown in FIG. 6. The offset parts of delay times caused by plane wave propagation are not subtracted from delay times in a graph shown in FIG. 9.

Hereinafter, the operation of the delay time generating unit 114 for discontinuity elimination will be concretely explained. In this case, the delay time generating unit 114 for discontinuity elimination generates delay times that asymptotically approaches the delay times caused by the forward diffracted wave 62 (shown by the curve 72) in the area B1 and the delay times caused by the backward diffracted wave 63 (shown by the curve 73) in the area B2 in this order as shown by the curve 91 in FIG. 6.

Here, in FIG. 4, FIG. 5, and FIG. 6, although the border between the area A and the area B, and the border between the area B and the area C are set as intersection points 34 between the reception scanning lines 31 and the outline of the irradiation area 32 of the transmission beam, it is not always necessary for the borders to correspond to the intersection points 34. By setting the area of the delay times caused by the diffracted waves in the area B wide, an SN ratio that is homogeneous all over the entirety of an image can be realized. Furthermore, if the area A and the area C are set too wide when the virtual source method is used, the gradient of the variation between delay times in the vicinity of the depth of the transit focus 33 becomes steep, and therefore the discontinuity in an image in the vicinity of the depth of the focus 33 is apt to become obvious. As a result, it is desirable to set the area of the delay times caused by the diffracted waves in the area B wide.

In this embodiment, the delay time generating unit 114 for discontinuity elimination generates delay times shown by the curve 91, which continuously connects the curve 72 of the delay times caused by the forward diffracted wave and the curve 73 of the delay times caused by the backward diffracted wave, from Expression (4) using Expression (3) that uses a sigmoid function defined below by Expression (2).

[Expression 2]

$$w_a(x) = \frac{1}{1 + e^{-ax}} \quad (2)$$

[Expression 3]

$$w_{single}(x) = \frac{1}{1 + e^{-a(x-x_f)}} \quad (3)$$

[Expression 4]

$$TOF_{approx.} = w_{single} \times TOF_{edge\_near} + (1 - w_{single}) \times TOF_{edge\_far} \quad (4)$$

The sigmoid function defined by Expression (2) is a function that asymptotically behaves at its both ends. Expression (3) is a function to which Expression (2) is applied, and a function of a depth x measured from the ultrasound element array 101 for defining a weighting factor w, where the range of x in Expression (3) is equal to the range of the area B, $x_f$ is a depth from the ultrasound element array 101 to the transmit focus 33, and $\alpha$ is a coefficient. Using Expression (3), a weighting function $w_{single}(x)$ is calculated whose value changes symmetrically on the shallow side and on the deep side of the transmit focus with the depth of the transmit focus 33 as a symmetric center. The shape of the weighting function $w_{single}(x)$ varies by changing the coefficient $\alpha$. In this embodiment, a predefined value or a value indicated from the control unit 111 is used as the coefficient $\alpha$. It is conceivable that the control unit 111 is configured to be able to accept the value of the coefficient $\alpha$ from an operator via the console 110.

The delay time generating unit 114 for discontinuity elimination weights $TOF_{edge\_near}$, which is a delay time (a time of flight) caused by the forward diffracted wave and a value shown by the curve 72, and $TOF_{edge\_far}$, which is a delay time (a time of flight) caused by the backward diffracted wave and a value shown by the curve 73, using the weighting function $w_{single}(x)$ obtained from Expression (3), and adds these weighted values as shown in Expression (4). Herewith, the delay time generating unit 114 for discontinuity elimination can generate delay times $TOF_{approx}$ (values shown by a curve 91) that asymptotically approach the curve 72 and the curve 73 respectively at its both ends as shown by the curve 91. To put it concretely, delay times shown by points o in FIG. 6 can be generated. Here, because a sigmoid-type function does not become zero at its ends, in order to match the values of $TOF_{approx}$ with the values shown by the curves 72 and 73 respectively at both ends of the area B, it is necessary to modify the values of $TOF_{approx}$ a little.

Although the sigmoid function is used as a model function that continuously connect the curve 72 and the curve 73 in the above Expressions (2) to (4), a function such as a generalized raised cosine-type function using a coefficient α, which is given by Expression (5), can be used instead of Expression (3). For example, a window function such as a Hanning function (Expression (6)), a Hamming function (Expression (7)), or the like can be used as one of such functions. In addition, the exponent of a cosine function part of a generalized cosine-type function can be 1 or more, for example, 2 or 4. By changing the exponent, the sharpness owing to the change of the coefficient of the function can be changed.

[Expression 5]

$$w(x)=\alpha-(1-\alpha)\cos(2\pi x) \quad (5)$$

[Expression 6]

$$w(x)=0.5-0.5\cos(2\pi x) \quad (6)$$

[Expression 7]

$$w(x)=0.54-0.46\cos(2\pi x) \quad (7)$$

Because the weighting functions given by the above Expressions (5) to (7) are cosine-type functions, the values of these functions become 0 or 1 at the ends of a target area, and therefore it is not necessary to modify the values at the ends. By defining the domain of Expressions (5) to (7) as $0 \le x \le 0.5$, functions that continuously vary from 0 to 1 can be realized. For example, by defining w(x) as shown by Expression (8), the curve 91 that continuously connects the both ends $x_{edge1}$ and $X_{edge2}$ of the area B can be realized. In Expression (8), $X_{edge1}$ and $x_{edge2}$ is the depths of the both ends of the area B on a certain scanning line as shown in FIG. 5 and FIG. 6.

[Expression 8]

$$w(x) = \alpha - (1-\alpha)\cos\left\{2\pi \frac{0.5(x - x_{edge1})}{(x_{edge2} - x_{edge1})}\right\} \quad (8)$$

Because the sigmoid function, that is, the abovementioned Expression (3), and Expressions (5) to (8) can be controlled by using only one parameter α respectively, only a little amount of calculation is required, and therefore these functions are advantageous in terms of the cost reduction and simplification of the implementation of hardware and software.

Furthermore, a weighting function w(x) can be defined not only by one of the abovementioned functions, but also by any of a Blackman window, a Kaiser window, and the like.

Hereinafter, the operations of the respective units of the reception beamformer 108 shown in FIG. 2 will be concretely explained. The delay time calculation unit 112 and the delay time generating unit 114 for discontinuity elimination include processing units such as CPUs and memories. After reading out and executing programs stored in advance in the memories, the delay time calculation unit 112 and the delay time generating unit 114 for discontinuity elimination operate on the basis of software processing. Alternatively, the delay time calculation unit 112 and the delay time generating unit 114 for discontinuity elimination can be comprised of pieces of hardware that execute predefined operations such as ASICs, FPGAs, and registers. Output values for each of transmission conditions, for each of depths, or for each of coefficients α are stored in advance in the registers. After the ASICs or FPGAs read out appropriate values corresponding to a condition from the registers, the delay time calculation unit 112 and the delay time generating unit 114 for discontinuity elimination operate. In addition, it is also possible that parts of the delay time calculation unit 112 and the delay time generating unit 114 for discontinuity elimination are realized by software processing and the other parts are realized by hardware.

The scanning line setting unit 116 of the reception beamformer 108 receives a transmission condition, the number and position information of scanning lines 31 from the control unit 111, and sets the predefined number of reception scanning lines 31 in the area 32 to which the transmission beam is irradiated as shown in FIG. 4.

In the case where the operation of the delay time calculation unit 112 is realized by software processing, the delay time calculation unit 112 calculates the outline of the irradiation area 32 using the transmission condition received from the control unit 111, calculates the positions of intersection points 34 between the outline of the irradiation area 32 and the reception scanning lines 31, and sets inner areas A and C and an outer area B on the reception scanning lines 31 with these intersection points as boundaries. On the other hand, in the case where the delay time calculation unit 112 is configured by hardware, data showing the ranges of the inner areas A and C, and the ranges of the outer area B for respective transmission conditions are calculated in advance with reference to the positional relationship between the shape of the irradiation area 32 and the reception scanning lines 31, and the data are stored in registers or memories according to the respective transmission conditions. The delay time calculation unit 112 reads out the ranges of the areas A, B, and C corresponding to a transmission condition, which are received from the control unit 111, and the set reception scanning lines 31 from the registers or memories, and outputs these ranges.

Furthermore, the delay time calculation unit 112 includes a register and a memory. Values on the curve 71 of the delay times of the area A, values on the curve 72 of the delay times of the area B1, values on the curve 73 of the delay times of the area B2, and values on the curve 74 of the delay times of the area C are stored in advance according to the respective transmission conditions, the respective reception scanning lines 31, or the positions of the respective ultrasound elements 105 in the register and memory. The delay time calculation unit 112 reads out delay times regarding plural points (segment nodes) of the reception scanning lines 31 in the areas A and C according to the respective transmission conditions, the respective reception scanning line 31, and the positions of the respective ultrasound elements 105 from the register or the memory.

Figure 10:
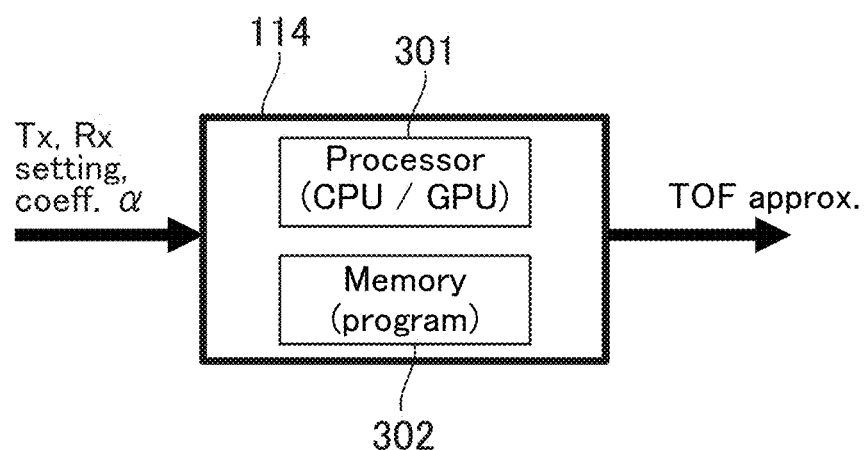
FIG. 10 is a block diagram showing a configuration example for realizing the operation of a delay time generating unit 114 for discontinuity elimination of the second embodiment in a software-based way using a processor 301 and a memory 302.

The delay time generating unit 114 for discontinuity elimination generates delay times regarding plural points (segment nodes) in the area B along the curve 91 for discontinuity elimination. To put it concretely, if the delay time generating unit 114 for discontinuity elimination is configured to include a processing unit 301 and a memory 302 as shown in FIG. 10, and its operation is realized by software processing, delay times for discontinuity elimination are generated by the operation of the delay time generating unit 114 for discontinuity elimination as described below. That is, the delay time generating unit 114 for discontinuity elimination calculates Expression (3) using a coefficient α, a range of the depth x of the area B, and the depth of the transmit focus 33 that are received from the control unit 111 and the scanning line setting unit 116, and calculates a weighting function $w_{single}(x)$ for each depth x. Next, the delay time generating unit 114 for discontinuity elimination reads out the delay time $TOF_{edge\_near}$ on the curve 72 in the area B1 and $TOF_{edge\_far}$ on the curve 73 in the area B2 from the register and the memory of the delay time calculation unit 112. Expression (4) is calculated using the weighting function $w_{single}(x)$, the delay time $TOF_{edge\_near}$, and $TOF_{edge\_far}$ to obtain a delay time for discontinuity elimination $TOF_{approx}$ for each depth x. Here, as mentioned above, any of Expressions (5) to (7) can be used instead of Expression (3). In addition, because the gradient of the curve 91 is steep, it is desirable to set distances between segment nodes in the area B shorter than distances between segment nodes in the areas A and C.

Furthermore, in the case where the delay time generating unit 114 for discontinuity elimination is configured with hardware as shown in FIG. 11(*c*), the hardware is configured to include registers 303 (refer to FIG. 11(*a*)) that store the values of the weighting function $w_{single}(x)$, which are calculated in advance for the combinations of coefficients α and the depths of the area B using Expression (3), according to the depths of the transmit focus 33. The delay time generating unit 114 for discontinuity elimination reads out a weighting function $w_{single}(x)$ corresponding to a coefficient α, a range of the depth x of the area B, and a depth of the transmit focus 33, which are received from the control unit 111 and the scanning line setting unit 116, from the plural registers 303. Next, the delay time generating unit 114 for discontinuity elimination reads out $TOF_{edge\_near}$ on the curve 72 in the area B1 and $TOF_{edge\_far}$ on the curve 73 in the area B2 from the register and the memory of the delay time calculation unit 112. The delay time generating unit 114 for discontinuity elimination calculates Expression (4) to obtain a delay time for discontinuity elimination $TOF_{approx}$ using these $TOF_{edge\_near}$, $TOF_{edge\_far}$, and the weighting function $W_{single}(x)$ for each depth x of a predefined segment point in the area B. Here, the values of the weighting function $w_{single}(x)$, which are stored in advance in the registers 303, can be calculated using any of Expressions (5) to (7) instead of Expression (3).

In addition, the configuration of the delay time calculation unit 111 is not limited to the configuration including plural registers 303 in which all the values corresponding to all combinations of conditions are stored as shown in FIG. 11(*c*), and the configuration including registers whose number is less than the number of all the combinations of conditions, and an interpolation circuit 304 that calculates a weighting function $w_{single}(x)$ corresponding to a required condition using values stored in the registers 303 by means of interpolation calculation can be utilized as shown in FIG. 11(*b*). For example, the interpolation circuit 304 can be realized using pieces of hardware such as FPGA. Herewith, the circuit size shown in FIG. 11(*c*) can be reduced.

The delay time calculation unit 112 and the delay time generating unit 114 for discontinuity elimination transfer delay times calculated regarding plural segment points in the areas A, B, and C to the delay time memory 123. Delay times are set for each ultrasound element 105 regarding one reception scanning line 31.

The delaying/adding/phasing unit 204 reads out delay times and position information for the respective segment nodes from the delay time memory 123, and calculates delay times at the positions of reception phasing points between segment nodes on a reception scanning line using interval linear interpolation calculation. After received signals at each ultrasound element 105 are delayed using the calculated delay times, and the delayed received signals are phased, these signals are added together to obtain a phased signal. Because delay times that continuously change are set in the outer area B by the curve 91, the values of phased signals also become continuous.

This is executed regarding all the reception scanning lines 31. Phased signals calculated regarding reception phasing points of each reception scanning line 31 are stored in the beam memory 206. The above operation is repeated a predefined times while the irradiation position of the transmission beam is changed.

The inter-transmission synthesis unit 205 reads out plural phased signals at the same phasing point from the beam memory 206, and synthesizes the read-out phased signals to perform aperture synthesis. Next, using the synthesized phased signals, an image in the imaged area is generated. The generated image is stored in the frame memory 207, and at the same time it is output to the image processing unit 109. The image processing unit 109 displays the image, on which image processing is executed as required, on the image display unit 103.

The displayed image does not generate a discontinuous artifact even in the vicinity of the transmit focus, and can display a highly accurate image.

Third Embodiment

In a third embodiment, the delay time generating unit 114 for discontinuity elimination generates the curve 92 (refer to points A in FIG. 6) that continuously connects the curve 72 of delay times caused by a forward diffracted wave and the curve 73 of delay times caused by a backward diffracted wave using below Expressions (9-1), (9-2), (10-1), and (10-2).

As is clear from FIG. 6, the curve 92 is a two-step curve that has a part (B1) connecting the curve 72 showing the variation between delay times in the shallow area B1 and a straight line 75 showing the variation between delay times determined on the basis of plane wave propagation, and a part (B2) connecting the straight line 75 based on the plane wave propagation and the curve 73 showing the variation between delay times in the deep area B2.

Both Expressions (9-1) and (9-2) are expressions used for determining weighting functions using a sigmoid function as is the case of Expression (3). In this embodiment, an area B is divided into the area B1 and the area B2 with the transmit focus as a boundary between the areas B1 and B2, and Expression (9-1) and Expression (9-2) are used for generating weighting functions for the area B1 and area B2 respectively. Here, in Expression (1), x1 is the depth of a middle point between the edge of the area B on the side of the area A and the depth of the transmit focus (focus), and x2 is the depth of a middle point between the depth of the transmit focus (focus) and the edge of the area B on the side of the area C. Here, the range of x used in Expressions (9-1), (9-2), (10-1), and (10-2) is equal to the range of the area B.

By calculating Expressions (10-1) and (10-2) using the weighting functions $w_{double}(x)$ obtained from Expressions (9-1) and (9-2), the delay times (times of flight) $TOF_{edge\_near}$ (the values of the curve 72) caused by the forward diffracted wave, the delay times $TOF_{PW}$ (the values of the straight line 75) caused by plane wave propagation, and the delay times (time of flight) $TOF_{edge\_far}$ (the values of the curve 73) caused by the backward diffracted wave are respectively weighted and added. Herewith, the delay time generating unit 114 for discontinuity elimination can generates the delay times $TOF_{approx}$ (the curve 92), which crosses the straight line 75 based on plane wave propagation after asymptotically approaching the curve 72, and then asymptotically approaches the curve 73, as shown by the curve 92.

[Expression 9]

$$w_{double}(x) = \begin{cases} \dfrac{1}{1+e^{-a(x-x_1)}}: & x \leq x_f \quad (9-1) \\ \dfrac{1}{1+e^{-a(x-x_2)}}: & x > x_f \quad (9-2) \end{cases}$$

[Expression 10]

(i) $x \leq x_f$ $$TOF_{approx.} = w_{double}(x) \times TOF_{edge\_near} + (1 - w_{double}(x)) \times TOF_{PW} \quad (10-1)$$

(ii) $x > x_f$ $$TOF_{approx.} = w_{double}(x) \times TOF_{PW} + (1 - w_{double}(x)) \times TOF_{edge\_far} \quad (10-2)$$

Furthermore, using cosine-type functions in Expressions (11-1) and (11-2) also in this case makes it possible to generate delay times $TOF_{approx}$ (the curve 92), which crosses the straight line 75 based on plane wave propagation after asymptotically approaching the curve 72, and then asymptotically approaches the curve 73, as shown by the curve 92. In other words, the curve 92 that can continuously connect both ends $X_{edge1}$ and $X_{edge2}$ of the area B can be realized. In Expression (11-1) and Expression (11-2), $X_{edge1}$ and $x_{edge2}$ are the depths of both ends of the area B on a certain scanning line as shown in FIG. 5 and FIG. 6, and $x_f$ is the depth of the transmit focus.

[Expression 11]

$$w(x) = \alpha - (1-\alpha)\cos\left\{2\pi \dfrac{0.5(x - x_{edge1})}{(x_f - x_{edge1})}\right\}: x \leq x_f \quad (11-1)$$

$$w(x) = \alpha - (1-\alpha)\cos\left\{2\pi \dfrac{0.5(x - x_f)}{(x_{edge2} - x_f)}\right\}: x > x_f \quad (11-2)$$

Other configurations, operations, and advantageous effects of the third embodiment are similar to those of the second embodiment, so descriptions about them will be omitted. However, the operations of the delay time calculation unit 112 and the delay time generating unit 114 for discontinuity elimination can be also realized by means of software. Alternatively, the operations of the delay time calculation unit 112 and the delay time generating unit 114 for discontinuity elimination can be also realized by means of hardware.

Fourth Embodiment

An ultrasound image pickup apparatus of a fourth embodiment will be explained below.

Figure 12:
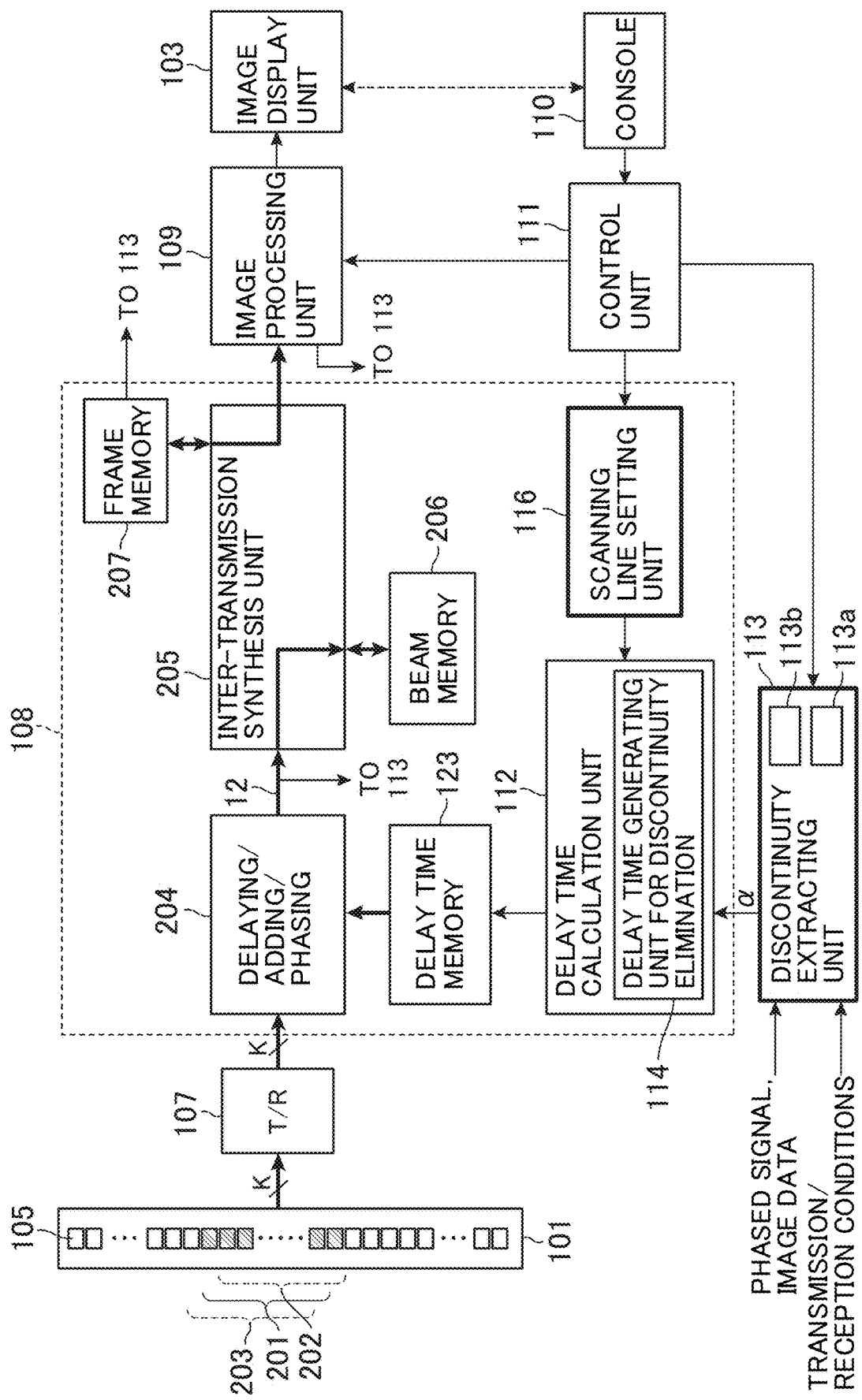
FIG. 12 is a block diagram showing the configuration of the reception beamformer of an ultrasound image pickup apparatus of a fourth embodiment.

As shown in FIG. 12, the ultrasound image pickup apparatus of the fourth embodiment includes a discontinuity extracting unit 113. The discontinuity extracting unit 113 includes a detection unit 113a that detects whether or not discontinuity has been generated in phased signals and the like, and an optimal coefficient setting unit 113b that continues changing delay times generated by a delay time generating unit 114 for discontinuity elimination until the degree of discontinuity becomes equal to or less than a predefined value.

Figure 13:
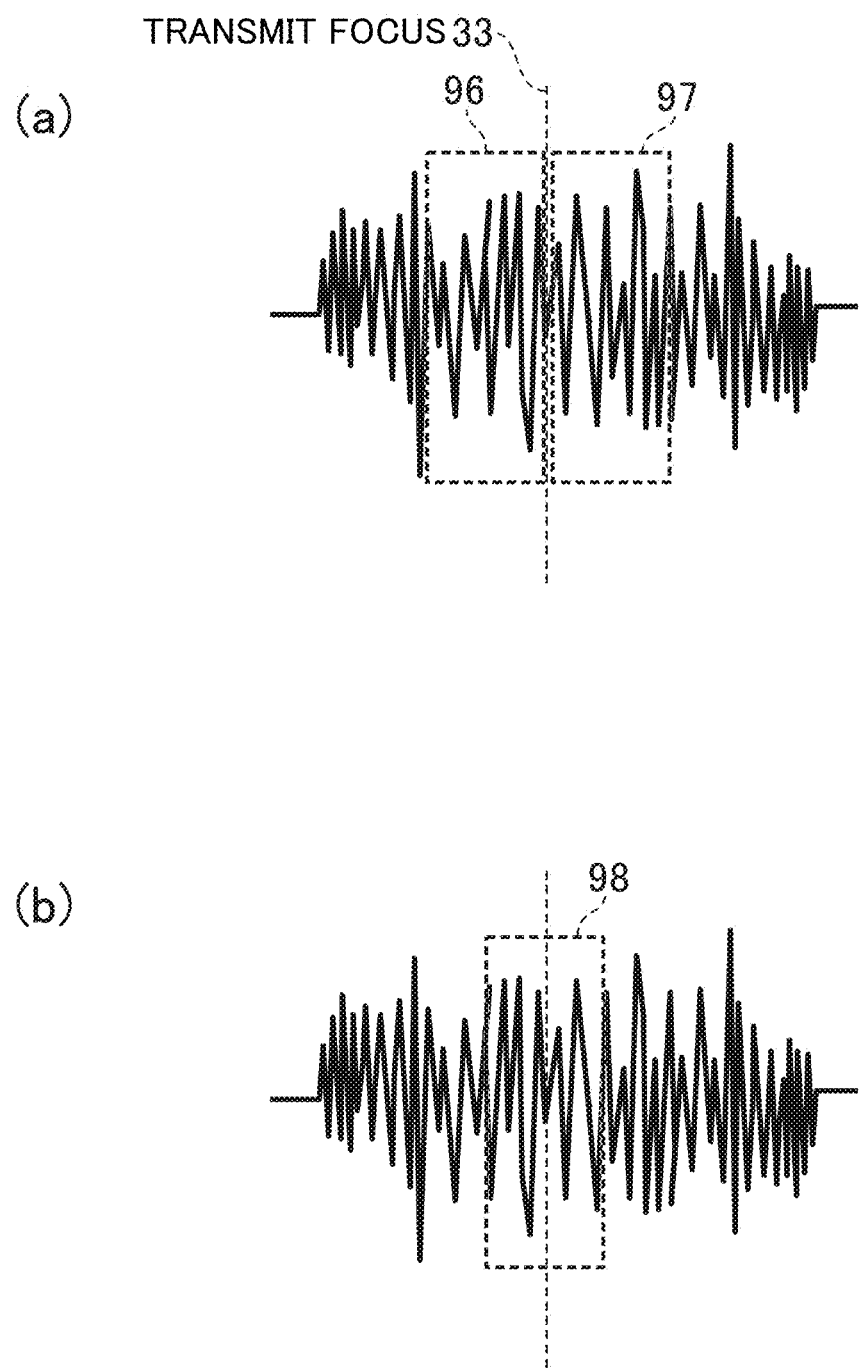
FIGS. 13(a) and (b) are explanatory diagrams showing the operation of a detection unit 113a of the fourth embodiment that detects the degree of discontinuity.

The detection unit 113a of the discontinuity extracting unit 113 receives phased signals in front of and at the rear of a transmit focus 33 from a delaying/adding/phasing unit 204, and sets two areas 96 and 97 between which the transmit focus 33 is sandwiched as phased signals as shown in FIG. 13(a). It will be assumed that the width of the depth of the area 96 and the width of the depth of the area 97 have predefined values respectively. Next, as an index showing the degree of discontinuity between the phased signal in the area 96 and the phased signal in the area 97, a correlation coefficient (for example, a pearson's correlation coefficient or the coefficient of the maximum value of the cross-correlation function calculated by convolution operation at sample points within the range of the depth of the area 96 plus the depth of the area 97) between the two phased signals is calculated. If the value of the calculated correlation coefficient is equal to or less than a predefined value (for example, if the value is 0.95 or 0.8 assuming the maximum value of the correlation coefficient is 1.0), the detection unit 113a judges that discontinuity is generated, and instructs the optimal coefficient setting unit 113b to calculate an optimal coefficient.

Furthermore, after setting an area 98, which includes the transmit focus 33 and has a predefined depth width, as a phased signal as shown in FIG. 13(b), the detection unit 113a can also calculate the differential coefficients and statistical quantities of the phased signal in the area 98 instead of the correlation function. If the calculated differential coefficients are equal to or larger than a predefined value (for example, if the calculated differential coefficients are ten times the average value of already-calculated differential coefficients in an area having moderate differential coefficients such as the area A or C), the detection unit 113a judges that the degree of discontinuity larger than a predefined value is generated. In addition, the value of the variance of the phased signals or the rank of the correlation matrix calculated from the phased signals can be used as one of the statistical quantities. If the statistical quantity is near to a desired value, it is judged that the degree of discontinuity is small, and if the statistical quantity is displaced from the desired value by a predefined value or more, it is judged that the degree of discontinuity is larger than a predefined value.

The operation of the above detection unit 113a can be realized by configuring the detection unit 113a with a processing unit and a memory, and by executing software processing in which the processing unit reads out programs stored in the memory and executes the programs.

Figure 14:
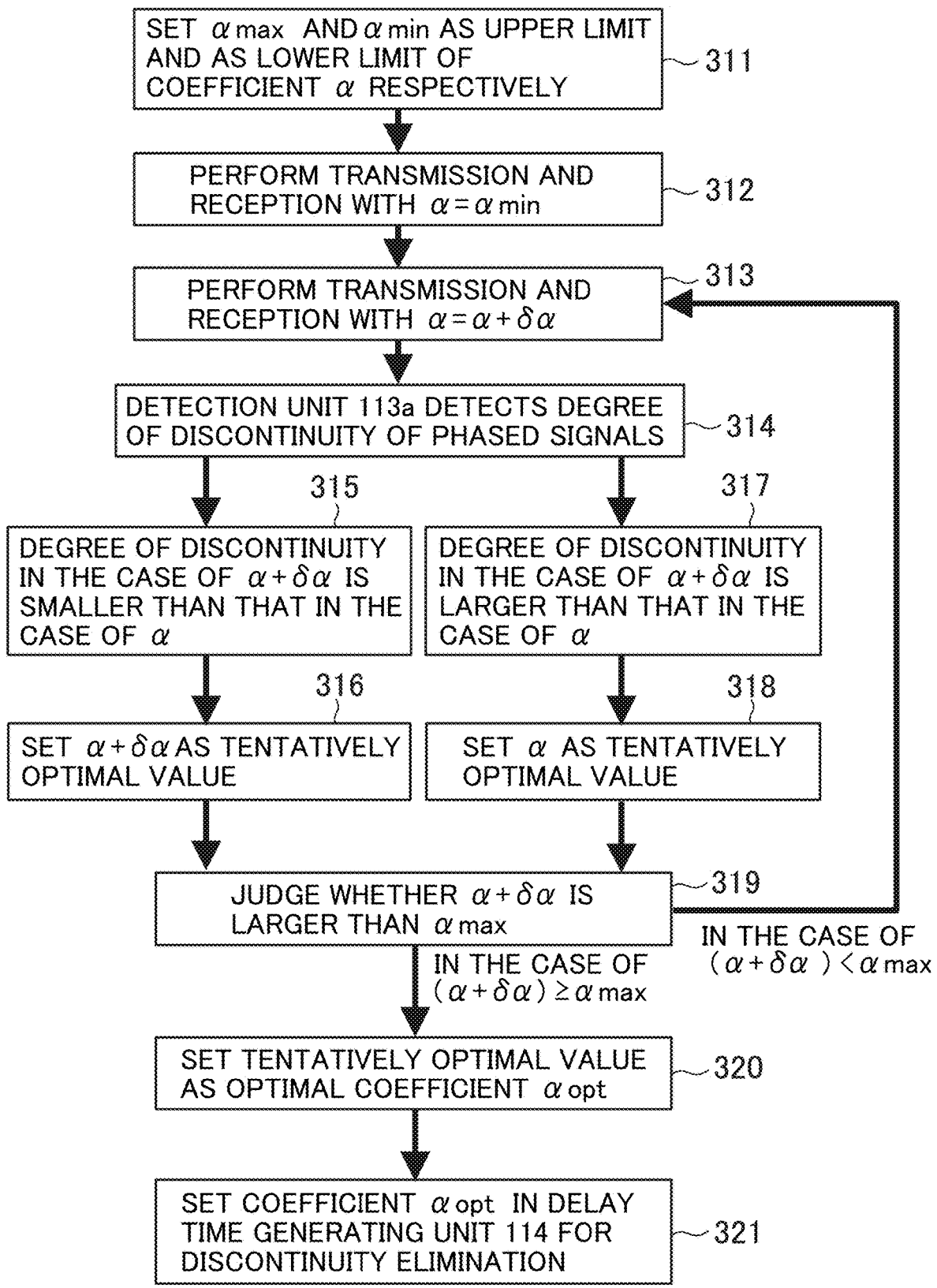
FIG. 14 is a flowchart showing the operation of an optimal coefficient setting unit 113b of the fourth embodiment.

If the degree of discontinuity detected by the detection unit 113a is larger than the predefined value, the optimal coefficient setting unit 113b operates as shown by a flowchart in FIG. 14 and reassigns an appropriate value to the coefficient α used in the abovementioned Expression (3) and the like. To put it concretely, first the optimal coefficient setting unit 113b sets the lower limit value αmin and the upper limit value αmax of the coefficient α (at step 311). The upper limit value αmax and the lower limit value αmin can be predefined values or can be values that the control unit 111 receives from an operator via the console 110.

Next, after the lower limit value αmin is assigned to a, the transmission/reception of ultrasound waves between the detection unit 113a and a test object 100 or a phantom is performed with a predefined transmission condition and a predefined reception condition respectively under the control by the control unit 11 (at step 312). The reception beamformer 108 executes reception beamforming. The detection unit 113a detects the degree of discontinuity regarding phased signals obtained by this transmission/reception, and stores the result in the memory (at step 314).

Next, after α+δα is assigned to α (where δ is a predefined coefficient), transmission/reception is performed (at step 313), and the detection unit 113a detects the degree of discontinuity regarding the phased signals, so that the result is stored in the memory (at step 314). Subsequently, the degree of discontinuity in the case of the previous coefficient α and the degree of discontinuity in the case of a new coefficient α+δα is compared with each other, and if the degree of discontinuity in the case of the new coefficient α+δα is smaller, the new coefficient α+δα is stored in the memory as a tentatively optimal value, and if the degree of discontinuity in the case of the new coefficient α+δα is larger, the previous coefficient α is stored in the memory as a tentatively optimal value (at step 315 to 318). Next, the flow goes back to step 313, and δα is added to the current coefficient α, and the above steps 314 to 318 are repeated. After the above procedure is repeated until α+δα becomes equal to or more than αmax (at step 319), the optimal coefficient αopt that makes the degree of discontinuity of the phased signals the smallest can be obtained by assigning the tentatively optimal value α to αopt (at step 320). The obtained optimal coefficient αopt is set in the delay time generating unit 114 for discontinuity elimination (step 321).

Through the above-described steps, because whether discontinuity is generated or not can be examined, and furthermore, an optimal coefficient α that does not cause discontinuity between actual phased signals can be set, an image can be generated by performing transmission/reception under the condition that a discontinuity between phased signals does not generated owing to a discontinuity of delay times.

Here, although the abovementioned optimal coefficient setting unit 113b obtains an optimal coefficient αopt by actually repeating the transmission/reception, a register 151, in which optimal coefficients α are stored after the optimal coefficients α are calculated according to respective transmission conditions (such as transmit focuses 33) and respective reception conditions (such as the positions of reception scanning lines) in advance, can be used as the optimal coefficient setting unit 113b (refer to FIG. 15(b)). In this case, the optimal coefficient setting unit 113b reads out an optimal coefficient α according to a transmission condition and a reception condition received from the control unit 111 from the register 151, and outputs the optimal coefficient α. The output coefficient α is set in the delay time generating unit 114 for discontinuity elimination. In this case, if the delay time generating unit 114 for discontinuity elimination includes registers 303 in each of which the relationship of an α and an x is stored as shown in FIG. 11(c), it is also possible to dispose the register 151 in the delay time generating unit 114 for discontinuity elimination after combining the registers 303 with the register 151 shown in FIG. 15(b) (refer to FIG. 15(a)).

Fifth Embodiment

In an ultrasound image pickup apparatus of a fifth embodiment, a detection unit 113a of a discontinuity extracting unit 113 detects the degree of discontinuity in the vicinity of the depth of a transmit focus 33 using image data generated by a reception beamformer 108. As the image data, image data that is synthesized by aperture synthesis and is stored in the frame memory 207 shown in FIG. 12 of the fourth embodiment, or image data, on which image processing is executed by the image processing unit 109, are used. In addition, image data that is generated without being synthesized by aperture synthesis can be also used as the image data.

Figure 16:
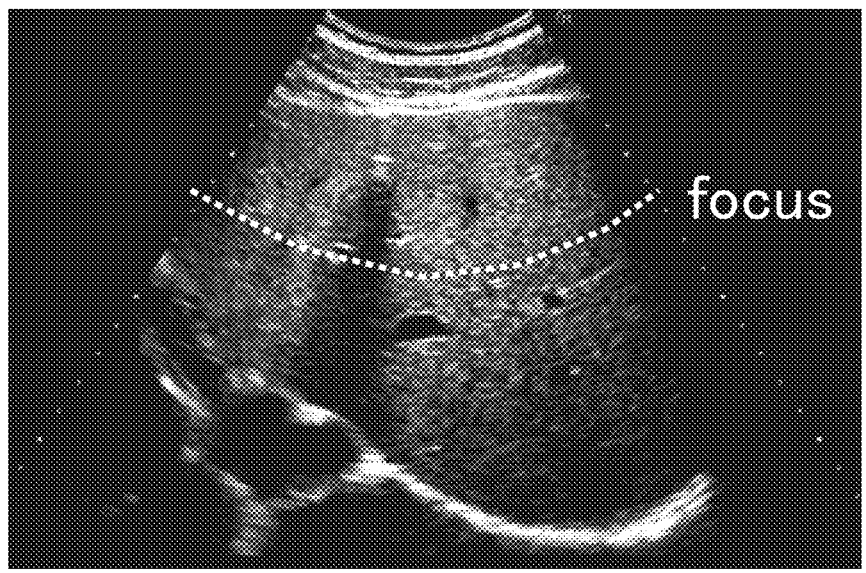
FIG. 16 is an explanatory diagram showing an image data and the position of the depth of a transmit focus used in a fifth embodiment.

The detection unit 113a extracts statistical quantities in the vicinity of the transmit focus 33 regarding image data such as that shown in FIG. 16. The entropy of an image is used as one of the statistical quantities. If the entropy of an image in the vicinity of the transmit focus 33 is smaller than a predefined value, it is judged that the degree of discontinuity is equal to or larger than a predefined value. An optimal coefficient setting unit 113b sets a coefficient α so that the entropy of the image becomes the maximum.

Because other configurations are the same as those described in the fourth embodiment, explanations about those configurations will be omitted.

LIST OF REFERENCE SIGNS

100: Test Object
101: Ultrasound Element Array
102: Ultrasound Image Pickup Apparatus Body
103: Image Display Unit
104: Transmission Beamformer
106: Ultrasound Probe
107: Transmission/Reception Separation Circuit (T/R)
108: Reception Beamformer
109: Image Processing Unit
110: Console
111: Control Unit
112: Delay Time Calculation Unit
113: Discontinuity Extracting Unit
114: Delay Time Generating Unit For Discontinuity Elimination
116: Scanning Line Setting Unit
123: Delay Time Memory

The invention claimed is:

1. An ultrasound image pickup apparatus comprising:
an ultrasound element array in which a plurality of ultrasound elements are arranged in a predefined direction;
a transmission beamformer that makes at least some of the plurality of ultrasound elements transmit a focusing-type transmission beam to the imaged area of a test object; and
a reception beamformer that delays reception signals output by the plurality of ultrasound elements, which receive ultrasound waves from the test object, by delay times to phase the reception signals, and outputs phased signals after adding the delayed and phased reception signals,
wherein the reception beamformer includes at least one non-transitory computer readable medium and at least one processor, the at least one non-transitory computer readable medium comprising instructions that when executed by the at least one processor enable the reception beamformer to perform the steps of:
setting reception scanning lines not only inside of the irradiation area of the focusing-type transmission beam but also outside of the irradiation area of the focusing-type transmission beam; and
calculating the delay times at predefined points on the reception scanning lines,
calculating the delay times on the reception scanning lines outside of the irradiation area in a shallow area on the shallow side of the transmit focus of the transmission beam on the basis of the waveform of a diffracted wave from one end of the plurality of ultrasound elements that irradiate the transmission beam, and calculating the delay times on the reception scanning lines outside of the irradiation area in a deep area on the deep side of the transmit focus of the transmission beam on the basis of the waveform of a diffracted wave from the other end, and generating, for discontinuity elimination, the delay times that connect the delay times in the shallow area and the delay times in the deep area in a vicinity of a depth of the transmit focus, wherein the delay times are generated using the following expression:

$$\text{TOF}_{approx} = W_{single}(X) \times \text{TOF}_{edge\_near} + (1 - W_{single}) \times \text{TOF}_{edge\_far} \quad (4)$$

where, x is a range corresponding to the shallow area and the deep area of the transmit focus, $w_{single}(x)$ is a weighting factor, $\text{TOF}_{edge\_near}$ is a delay time caused by a forward diffracted wave, and $\text{TOF}_{edge\_far}$, which is a delay time caused by the backward diffracted wave using the weighting function $w_{single}(x)$, and $\text{TOF}_{approx}$ is a delay time that asymptotically approach curves caused by the forward reflected wave ($\text{TOF}_{edge\_near}$) and the backward deflected wave ($\text{TOF}_{edge\_far}$).

2. The ultrasound image pickup apparatus according to claim 1, wherein the reception beamformer further performs the step of generating, for discontinuity elimination, the delay times whose values vary in a curved line in the depth direction in order to connect the delay times in the shallow area and the delay times in the deep area.

3. The ultrasound image pickup apparatus according to claim 1, wherein the reception beamformer further performs the step of generating, for discontinuity elimination, the delay times that connect the discontinuity by respectively multiplying the delay times in the shallow area and the delay times in the deep area with weights and by adding these weighted delay times.

4. The ultrasound image pickup apparatus according to claim 3, wherein the weights are set in such a way that the delay times in the vicinity of the depth of the transmit focus asymptotically approach the variation in the direction of the depth of the delay times in the shallow area and the variation in the direction of the depth of the delay times in the deep area.

5. The ultrasound image pickup apparatus according to claim 2, wherein a curve of the delay times generated for discontinuity elimination include:
   a part that connects a curve showing the variation between the delay times in the shallow area and a straight line showing the variation between delay times determined on the basis of plane wave propagation; and
   a part that connects the straight line regarding the plane wave propagation and the curve showing the variation between the delay times in the deep area.

6. The ultrasound image pickup apparatus according to claim 1, further comprising at least one other non-transitory computer readable medium and at least one other processor, the at least one other non-transitory computer readable medium comprising instructions that when executed by the at least one other processor enable the ultrasound image pickup apparatus to perform the step of:
   detecting the degree of discontinuity of the wave fronts of the phased signals in the vicinity of the depth of the transmit focus,
   wherein, for discontinuity elimination, the delay times to be generated are changed if the degree of discontinuity is larger than a predefined value.

7. The ultrasound image pickup apparatus according to claim 1, further comprising at least one other non-transitory computer readable medium and at least one other processor, the at least one other non-transitory computer readable medium comprising instructions that when executed by the at least one other processor enable the ultrasound image pickup apparatus to perform the steps of:
   generating an image using the phased outputs which are output by the reception beamformer; and
   detecting the degree of discontinuity in the image in the vicinity of the depth of the transmit focus of the image,
   wherein, for discontinuity elimination, the delay times to be generated are changed if the degree of discontinuity is larger than a predefined value.

8. The ultrasound image pickup apparatus according to claim 6, wherein a correlation function between the phased signals before and after the depth of the transmit focus is used, or the differential coefficients or the variance value of the phased signals in the vicinity or neighborhood of the depth of the transmit focus are used as the degree of discontinuity.

9. The ultrasound image pickup apparatus according to claim 7, wherein the entropy of the image in the vicinity of the depth of the transmit focus is used as the degree of discontinuity.

10. The ultrasound image pickup apparatus according to claim 6, wherein the delay times are repeatedly changed until the detected degree of discontinuity becomes a predefined value or less.

11. The ultrasound image pickup apparatus according to claim 1, wherein the reception beamformer is a beamformer that performs aperture synthesis processing, and includes:
    a memory that stores the phased signal for each transmission; and
    further performs the steps of selecting phased signals regarding the same point from the phased signals stored in the memory for respective transmissions, and synthesizing the selected phased signals.

12. The ultrasound image pickup apparatus according to claim 1, wherein the delay times are generated to asymptotically approach first delay times caused by a forward diffracted wave in a first area and second delay times caused by a backward diffracted wave in a second area in that order.

13. The ultrasound image pickup apparatus according to claim 1, wherein the delay times are generated using the following additional expressions:

$$\text{tof} = (d_1 \pm d_2 + d_3)/C \quad (1)$$

$$w_a(x) = \frac{1}{1 + e^{-ax}} \quad (2)$$

$$w_{single}(x) = \frac{1}{1 + e^{-a(x - x_f)}} \quad (3)$$

where expression (3) can be substituted by any of the following expressions (5)-(7):

$$w(x) = \alpha - (1 - \alpha)\cos(2\pi x) \quad (5)$$

$$w(x) = 0.5 - 0.5\cos(2\pi x) \quad (6)$$

$$w(x) = 0.54 - 0.46\cos(2\pi x) \quad (7)$$

where, $D_1$ is a distance from the center of a transmission aperature to a virtual source, $d_2$ is a distance from the virtual source to a reception phasing point, $d_3$ is a distance between the receptio phasing point and a reception ultrasound element, C is the speed of sound in a medium, x is a range corresponding to the shallow area and the deep area of the transmit focus, w(x) and $w_{single}(x)$ are weighting functions, $x_f$ is a depth from the ultrasound element array to the transmit focus, α is a coefficient (also shown as "a") that varies the shape of the weighting function $W_{single(X)}$, and TOF is a time of flight of a sound wave using a virtual source method.

* * * * *